US012697411B2

(12) United States Patent
Nebot Troyano et al.

(10) Patent No.: US 12,697,411 B2
(45) Date of Patent: Aug. 4, 2026

(54) IN-SITU FILM-FORMING COMPOSITION

(71) Applicant: LABORATORIOS INIBSA, S.A., Lliçà de Vall (ES)

(72) Inventors: Joaquín Nebot Troyano, Molins de Rei (ES); Ramon M. Roca I Juanes, Barcelona (ES)

(73) Assignee: LABORATORIOS INIBSA, S.A., Llica de Vall (ES)

( * ) Notice: Subject to any disclaimer, the term of this patent is extended or adjusted under 35 U.S.C. 154(b) by 311 days.

(21) Appl. No.: 18/559,199

(22) PCT Filed: May 6, 2022

(86) PCT No.: PCT/EP2022/062272
§ 371 (c)(1),
(2) Date: Nov. 6, 2023

(87) PCT Pub. No.: WO2022/234081
PCT Pub. Date: Nov. 10, 2022

(65) Prior Publication Data
US 2024/0226369 A1      Jul. 11, 2024

(30) Foreign Application Priority Data

May 7, 2021    (EP) ..................................... 21382413

(51) Int. Cl.
| | |
|---|---|
| *A61L 24/00* | (2006.01) |
| *A61L 24/04* | (2006.01) |
| *A61L 24/10* | (2006.01) |
| *C08L 33/10* | (2006.01) |

(52) U.S. Cl.
CPC ......... *A61L 24/0015* (2013.01); *A61L 24/046* (2013.01); *A61L 24/10* (2013.01); *C08L 33/10* (2013.01); *A61L 2300/214* (2013.01); *A61L 2300/404* (2013.01); *A61L 2300/80* (2013.01); *A61L 2400/14* (2013.01); *C08L 2203/02* (2013.01)

(58) Field of Classification Search
CPC .... A61L 24/0015; A61L 24/046; A61L 24/10; A61L 2300/404; A61L 2300/80; A61L 2400/14; A61L 2300/214; C08L 33/10; C08L 2203/02
See application file for complete search history.

(56) References Cited

U.S. PATENT DOCUMENTS

| | | | |
|---|---|---|---|
| 7,842,749 B2 | 11/2010 | Shalaby et al. | |
| 2018/0000858 A1* | 1/2018 | Liang ................. | A61L 26/0019 |

FOREIGN PATENT DOCUMENTS

| | | | |
|---|---|---|---|
| RU | 2382653 C2 * | 2/2010 | ........... A61K 8/0208 |
| WO | 2007/005029 A2 | 1/2007 | |
| WO | 2017/030555 A1 | 2/2017 | |

OTHER PUBLICATIONS

Maluf et al. (J. of Applied Oral Science (2020); 28;e20190039 9 pages).*
Bianchera et al. (Expert Opinion on Therapeutic Patents 30(12) 2020.*
Labella-Lorite et al. (J. of Drug Delivery Science and Technology 59 (2020)101852.*
Demircan et al., "Effects of Lemon Essential Oil and Ethyl Lauroyl Arginate on the Physico-Chemical and Mechanical Properties of Chitosan Films for Mackerel Fillet Coating Application", Journal of Food Measurement and Characterization (2021) 15:1499-1508, https://doi.org/10.1007/s11694-020-00745-1.
European Pharmacopoeia 10.0, Ph. Eur. (10.4) 2.7.2 Microbiological Assay of Antibiotics, Jan. 2020:20702, pp. 262-267, (2020).
Method USP <51> Antimicrobial Effectiveness Testing, Preservative Challenge Test of May 1, 2018 included in the 2021 edition; DocId: 1_GUID-772FE032-8921-4345-810E-945EF5BF1B15_3_en-US.
International Search Report and Written Opinion of International Application No. PCT/EP2022/062272 dated Aug. 31, 2022, 20 pages.

* cited by examiner

*Primary Examiner* — Shirley V Gembeh
(74) *Attorney, Agent, or Firm* — CHRISMAN GALLO TOCHTROP LLC

(57) ABSTRACT

A composition including: (a) one or more alkyl acrylaor alkyl methacrylate based polymer film forming agents; (b) one or more $(C_1-C_6)$alkyl N(alpha)-$(C_{10}-C_{25})$alkanoyl-L-arginate disinfectant or a salt thereof; (c) a solvent system comprising: (c1) one or more water immiscible solvents selected from $(C_1-C_5)$alkyl-CO—O—$(C_1-C_6)$alkyl, (($C_1$-$C_6$)alkyl)$_3$Si—O—Si(($C_1$-$C_6$)alkyl)$_3$, $(C_1-C_5)$alkyl-O—$(C_2-C_5)$alkyl and a mixture thereof; (c2) acetone; and (c3) one or more $(C_2-C_3)$ alcohols and processes for its preparation. An adherent film, including: (a) one or more film forming agents; and (b) one or more disinfectants; and processes for its preparation.

19 Claims, No Drawings

IN-SITU FILM-FORMING COMPOSITION

CROSS-REFERENCE TO RELATED APPLICATIONS

This is a National Stage application of PCT International Application PCT/EP2022/062272, filed on May 6, 2022, which claims the benefit of European Patent Application EP21382413.9 filed on May 7, 2021, both of which are incorporated herein by reference in their entirety.

The present invention relates to the field of film forming compositions; particularly to in-situ adherent film forming compositions after their application onto a surface to be filmed; and the in-situ adherent film thus obtained. It also relates to processes for their preparation as well as to their uses as drug delivery systems, dressing or fixation agent.

BACKGROUND ART

Film-forming compositions have been widely disclosed in the state of the art for personal and healthcare applications, and as drug delivery systems. These compositions upon contact with a surface (such as skin/hair/nail) rapidly create a film appropriate for curing or alleviating skin/hair/nail diseases or conditions. The way of forming the films implies firstly, mixing the components and secondly, applying the mixture thus obtained onto the desired surface to be filmed. However, this method has some disadvantages, such as for example the fact that the user must be skilled to ensure adequate mixing of the appropriate amounts of the components and also the subsequent application of the appropriate amount of the mixed formulation to the surface. Further, this method can also be complicated to perform, due to the handling of the different components of the composition and their subsequent application, as well as the accuracy of the measurement of the amounts of the ingredients and final composition.

Thus, ready-to-use hydrocolloids films (dressings) have been developed for overcoming the problems mentioned above. These films are attached to a protecting layer that has to be released before its used/application in the target/injured surface. However, these dressings have still some disadvantages related to their adhesive properties. In fact, the use mode recommends warming up the dressings before use to ensure an appropriate adherence to the surface. Unfortunately, even the previous warming, the edges of the dressing remain still lifted, which means that they can be adhered to other surface (such as clothes) or get dirty from the common use (such as with water, sand and/or dust).

Due to this fact, compositions capable of in-situ forming films onto appropriate surfaces have been developed. In particular, liquid plastic compositions dissolved in organic solvents have been disclosed in the state of the art for forming in-situ films (dressings) onto the skin surface. When such liquid compositions are applied onto the skin, the solvents evaporate, and the film (dressing) is in-situ created remaining on the target/injured surface without the need to be handled by the user. These compositions are commonly use in form of spray or brush-painting. However, these compositions have some drawbacks. On one hand, the presence of organic solvents (such as ethylacetate) that promote the formation and dryness of the film, commonly cause discomfort (i.e. pain/stinging) and skin irritation (dermatitis) during the application compromising the appropriate formation of the film. On the other hand, the hydrophilic-lipophilic balance of the plastic compositions forming part of the composition limit the addition of further active ingredients into the composition, such as antibiotics, anti-inflammatory or anticoagulant active ingredients that can avoid/reduce (over)infection and/or can accelerate the curative process of the injured surface. Besides, some of these plastic compositions contain ingredients such as film-forming and/or stabilizing agents (i.e. silicones, phthalates) not recommended or, even worst, banned by health authorities due to their demonstrated toxicity.

Thus, from what is known in the art it is derived that there is still the need of developing a composition capable of forming an in-situ adherent film in a short period of time without causing discomfort to the user or irritation to the skin and having good physical properties (such as stability, flexibility, and permeability/transpiration) complying at the same time the strict requirements of health authorities.

SUMMARY OF INVENTION

Inventors have found that a composition comprising a combination of one or more film forming agents and one or more disinfectants dissolved in a solvent system that comprises the combination of one or more water immiscible solvents selected from the group consisting of $(C_1-C_6)$alkyl-$CO$—$O$—$(C_1-C_6)$alkyl, $((C_1-C_6)$alkyl$)_3$Si—$O$—$Si((C_1-C_6)$alkyl$)_3$, $(C_1-C_5)$alkyl-$O$—$(C_2-C_5)$alkyl and a mixture thereof; acetone; and one or more $(C_2-C_3)$ alcohols is capable of forming an in-situ homogeneous, adherent and biocompatible film onto a suitable surface having appropriate physical and mechanical properties as well as the suitable disinfectant activity (in particular, antimicrobial and antifungal activity) for being used as biocompatible dressing or biocompatible fixation agent. Furthermore, the composition of the invention includes only gentle components that comply with the requirements of health authorities without the need of phthalates or latex containing compounds.

As it is demonstrated in the experimental section, the composition of the invention is stable and non-corrosive at the commonly used temperature and relative humidity of the manufacturing process and storage in the conditioning packages (such as pressurized and non-pressurized spray containers). This is advantageous because the compositions of the invention can be storage without particular restrictions (for example without the need to store in a refrigerator) but also because are ease to handle (for example can be easily kept on hand in case of travelling) allowing a safer and more convenient use; and therefore, costless.

Furthermore, the composition of the invention can be easily applied by any method known in the art, such as for example spraying or brushing it onto the target surface. When the surface is a tissue, such as skin, its application does not cause discomfort (without pain and without itching or stinging on not injured skin) and/or irritation (dermatitis) of the filmed area. This is advantageous because it is appropriate for all types of tissues, and particularly all types of skins including children's skin and/or sensitive skin (having at the same time a not unpleasant smell. Furthermore, when it is applied the composition dries quickly, in case of being applied on the skin, it does not cause its dehydration due to its capacity of forming a protective film that instantly relieves pain and prevents friction, while creating an optimal environment to allow rapid regeneration of the skin, if needed; and at the same time maintaining the appropriate permeability/transpiration. In fact, the composition of the invention allows forming an in-situ adherent film with appropriate light stability and physico- and mechanical properties. It is demonstrated that the in-situ adherent film maintains its integrity even of being exposed to high level of lateral movement, twisting force, and great pressures. Furthermore, as it is demonstrated in the experimental section, the in-situ adherent film of the present invention allows perspiration of the skin without compromising the impermeability of the film to water. In fact, the adherent film of the invention is permeable to steam and humidity but impermeable to water having light protecting effect, thus preventing maceration of the treated area allowing at the same time bathing and personal hygiene. Therefore, the in-situ film obtained by the application of the present invention acts like a second skin. Besides, the application of the composition of the present invention onto a tissue, such as skin, prevent its injurance. In fact, the adherent film of the present application applied to non-injured skin allows preventing wound skin, burn skin, skin blisters, skin chafing and sunlight damage prevention among others.

On the other hand, due to the high adherence properties, the composition of the present invention is also useful as in-situ film fixation agent. It means that the in-situ film obtained by the application of the composition of the invention is appropriate as fixing agent, either between tissues or between tissues and medical/surgical material such as for example the fixation of catheters to the skin.

Therefore, to sum up, the inventors have found that the composition of the invention is capable of being used as film-forming agent, particularly as in-situ film forming agent. In fact, the film formed in situ by the application of the composition of the present invention is appropriate as biocompatible dressing having the function of a second skin, as biocompatible fixing agent or as drug delivery device.

Thus, the first aspect of the invention refers to a composition comprising: (a) one or more film forming agents; (b) one or more disinfectant; (c) a solvent system comprising: (c1) one or more water immiscible solvents selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, $(C_1-C_5)$alkyl-O—$(C_2-C_5)$alkyl and a mixture thereof; (c2) acetone; and (c3) one or more $(C_2-C_3)$ alcohols; (d) optionally one or more appropriate excipients or carriers; and (e) optionally one or more additional active ingredients.

Particularly, a composition comprising:
(a) one or more film forming agents;
(b) one or more disinfectant;
(c) a solvent system comprising:
(c1) one or more water immiscible solvents selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, $(C_1-C_5)$alkyl-O—$(C_2-C_5)$alkyl and a mixture thereof;
(c2) acetone; and
(c3) one or more $(C_2-C_3)$ alcohols;
(d) optionally one or more appropriate excipients or carriers; and
(e) optionally one or more additional active ingredients; wherein:
the one or more film-forming agents (a) are selected from the group consisting of $(C_1-C_6)$alkyl acrylate based polymers; $(C_1-C_6)$alkyl methacrylate based polymers; $(C_1-C_6)$alkoxy $(C_1-C_6)$alkyl acrylate based polymers; $(C_1-C_6)$alkoxy $(C_1-C_6)$alkyl methacrylate based polymers, hydroxy$(C_1-C_6)$alkyl acrylate, hydroxy$(C_1-C_6)$alkyl methacrylate; copolymers thereof; copolymers of one of $(C_1-C_6)$alkyl acrylate based polymers; $(C_1-C_6)$alkyl methacrylate based polymers; $(C_1-C_6)$alkoxy $(C_1-C_6)$alkyl acrylate based polymers; $(C_1-C_6)$alkoxy $(C_1-C_6)$alkyl methacrylate based polymers, hydroxy$(C_1-$ $C_6)$alkyl acrylate, hydroxy$(C_1-C_6)$alkyl methacrylate with methacrylic acid; copolymers of one of $(C_1-C_6)$ alkyl acrylate based polymers; $(C_1-C_6)$alkyl methacrylate based polymers; $(C_1-C_6)$alkoxy $(C_1-C_6)$alkyl acrylate based polymers; $(C_1-C_6)$alkoxy $(C_1-C_6)$alkyl methacrylate based polymers, hydroxy$(C_1-C_6)$alkyl acrylate, hydroxy$(C_1-C_6)$alkyl methacrylate with acrylic acid; copolymers of one of $(C_1-C_6)$alkyl acrylate based polymers; $(C_1-C_6)$alkyl methacrylate based polymers; $(C_1-C_6)$alkoxy $(C_1-C_6)$alkyl acrylate based polymers; $(C_1-C_6)$alkoxy $(C_1-C_6)$alkyl methacrylate based polymers, hydroxy$(C_1-C_6)$alkyl acrylate, hydroxy$(C_1-C_6)$alkyl methacrylate with acrylamide; mono-acrylates of glycols and poly glycols; mono-methacrylates of glycols and polyglycols; glycidyl acrylate based polymers; and glycidyl methacrylate based polymers with acrylamide; and
the one or more disinfectants (b) are $(C_1-C_6)$alkyl N(alpha)-$(C_{10}-C_{25})$alkanoyl-L-arginate or a salt thereof.

The second aspect of the invention refers to the use of the composition of the first aspect of the invention, as film-forming agent; particularly for forming an in-situ adherent film.

The third aspect of the invention refers to an adherent film obtainable in-situ by applying the composition of the first aspect of the invention over the surface to be filmed under such conditions that allows obtaining the film; particularly wherein the surface is a non-living surface.

It is also a part of the invention, processes for the preparation of the composition of the first aspect of the invention and the adherent film of the third aspect of the invention.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper endpoints of the range. Ranges given, such as weight, temperatures, times, weights, and the like, should be considered approximate, unless specifically stated.

The terms "percentage (%) by weight", "weight/weight %" and "w/w %" have the same meaning and are used interchangeable. They refer to the percentage of each ingredient of the composition in relation to the total weight of the composition.

As it is mentioned above, the first aspect of the invention is a composition that comprises: (a) one or more film forming agents as defined herein; (b) one or more disinfectants as defined herein; (c) a solvent system comprising: (c1) one or more water immiscible solvents selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, $(C_1-C_5)$alkyl-O—$(C_2-C_5)$alkyl and a mixture thereof; (c2) acetone; and (c3) one or more $(C_2-C_3)$ alcohols; (d) optionally one or more appropriate excipients or carriers; and (e) optionally one or more additional active ingredients.

The term "film-forming agent" refers to any compound capable of building a thin layer covering the area of application. This term includes without limitation either those compounds totally or partially chemically or biotechnological synthesized and those being naturally occurring. Examples of chemically synthesized film forming agents includes, but without limitation, polyvinylpyrrolidone, polyvinylalcohol acrylate copolymers, acrylate crosspolymer, acrylamides copolymers or acetyl triethyl citrate. Examples of naturally occurring or biotechnologically produced includes, but without limitation, hyaluronic acid, glucans, pullulan, *Acacia senegal* gum, *Acacia catechu* gum or *Acacia farnesiana* gum.

In an embodiment, the composition comprises one or more film forming agents (a) selected from the group consisting of ($C_1$-$C_6$)alkyl acrylate based polymers; ($C_1$-$C_6$) alkyl methacrylate based polymers; ($C_1$-$C_6$)alkoxy ($C_1$-$C_6$) alkyl acrylate based polymers; ($C_1$-$C_6$)alkoxy ($C_1$-$C_6$)alkyl methacrylate based polymers; hydroxy($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers; a copolymer comprising two or more selected from the group consisting of $C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$)alkoxy ($C_1$-$C_6$)alkyl methacrylate based polymers; hydroxy($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers; a copolymer comprising one selected from $C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$) alkoxy ($C_1$-$C_6$)alkyl methacrylate based polymers; hydroxy ($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers and methacrylic acid; $C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$) alkoxy ($C_1$-$C_6$)alkyl methacrylate based polymers; hydroxy ($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers and acrylic acid: and $C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$) alkoxy ($C_1$-$C_6$)alkyl methacrylate based polymers; hydroxy ($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers with acrylamide; poly(vinyl alcohol) based polymer; poly(urethane) based polymer; silicone based polymer; cellulose based polymer, and mixture thereof.

In an embodiment, the composition comprises one or more film forming agents (a) selected from the group consisting of wherein the one or more film-forming agents (a) are selected from the group consisting of ($C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$)alkoxy ($C_1$-$C_6$)alkyl methacrylate based polymers, hydroxy($C_1$-$C_6$)alkyl acrylate, hydroxy($C_1$-$C_6$)alkyl methacrylate; copolymers thereof; copolymers of one of ($C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$)alkoxy ($C_1$-$C_6$)alkyl methacrylate based polymers, hydroxy($C_1$-$C_6$)alkyl acrylate, hydroxy ($C_1$-$C_6$)alkyl methacrylate with methacrylic acid; copolymers of one of ($C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$)alkoxy ($C_1$-$C_6$)alkyl methacrylate based polymers, hydroxy($C_1$-$C_6$)alkyl acrylate, hydroxy($C_1$-$C_6$)alkyl methacrylate with acrylic acid; copolymers of one of ($C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$) alkoxy ($C_1$-$C_6$)alkyl methacrylate based polymers, hydroxy ($C_1$-$C_6$)alkyl acrylate, hydroxy($C_1$-$C_6$)alkyl methacrylate with acrylamide; mono-acrylates of glycols and poly glycols; mono-methacrylates of glycols and polyglycols; glycidyl acrylate based polymers; and glycidyl methacrylate based polymers with acrylamide; and mixture thereof; particularly ($C_1$-$C_6$)alkoxy ($C_1$-$C_6$)alkyl methacrylate based polymers.

In an embodiment, the composition comprises one or more film forming agents (a) selected from the group consisting of ($C_1$-$C_6$)alkoxy ($C_1$-$C_6$)alkyl methacrylate based polymer selected from the group consisting of selected from the group consisting of 2-ethoxyethyl methacrylate, 2-methoxyethyl methacrylate, 2-propyl methacrylate and a mixture thereof. In an embodiment, the composition comprises 2-ethoxyethyl methacrylate as film forming agent (a).

For the purpose of the invention, the term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl. The term alkoxy refers to an alkyl-O— group, wherein alkyl is as defined above.

For the purpose of the present invention, the term "disinfectant" encompasses both biocide agents and preservative agents. The term "preservative" refers to any compound that helps to preserve the quality, integrity, and longevity of the composition. The preservative decreases the likeliness or time frame for spoilage, and delay, decrease, or diminish microbial and fungi growth that could lead to bacteria or fungi production. The term "biocide" refers to any compound capable of killing, destroying, deteriorating, rendering harmless, preventing the action, or combating organisms. The term biocide includes bactericidal (against bacteria) and fungicidal compounds (against fungi).

In an embodiment, the composition comprises one or more disinfectant (b) selected from the group consisting of ($C_1$-$C_6$)alkyl N(alpha)-($C_{10}$-$C_{25}$)alkanoyl-L-arginate or a salt thereof; chlorhexidine or a salt thereof; 2-fenoxietanol; sorbic acid and sorbates thereof; and a mixture thereof.

In an embodiment, the composition comprises a ($C_1$-$C_6$) alkyl N(alpha)-($C_{10}$-$C_{25}$)alkanoyl-L-arginate or a salt thereof as a disinfectant (b). In an embodiment, the composition comprises a ($C_1$-$C_6$)alkyl lauroyl arginate or a salt thereof as a disinfectant (b). In an embodiment, the composition comprises ethyl lauroyl arginate or a salt thereof as a disinfectant (b). In an embodiment, the composition comprises ethyl lauroyl arginate or a salt thereof as a disinfectant (b) selected from the group consisting of ethyl lauroyl hydrochloride salt, ethyl lauroyl hydrobromide salt, ethyl lauroyl arginate monolaurate, ethyl lauroyl arginate palmitate, ethyl lauroyl arginate stearate, ethyl lauroyl arginate lactate, ethyl lauroyl arginate citrate, ethyl lauroyl arginate oleate, ethyl lauroyl arginate benzoate, ethyl lauroyl arginate acetate, ethyl lauroyl arginate hydrogen sulfate and ethyl lauroyl arginate phosphonates; particularly ethyl lauroyl arginate hydrochloride salt.

In an embodiment, the composition of the invention comprises:

(a) one or more film forming $(C_1-C_6)$alkoxy $(C_1-C_6)$ alkyl methacrylate polymers; and (b) one or more $(C_1-C_6)$alkyl N(alpha)-$(C_{10}-C_{25})$alkanoyl-L-arginate disinfectants or a salt thereof.

In an embodiment, the composition of the invention comprises:

(a) one or more film forming $(C_1-C_6)$alkoxy $(C_1-C_6)$ alkyl methacrylate polymers selected from the group consisting of 2-ethoxyethyl methacrylate, 2-methoxyethyl methacrylate, 2-propyl methacrylate and a mixture thereof; and (b) one or more $(C_1-C_6)$alkyl N(alpha)-$(C_{10}-C_{25})$alkanoyl-L-arginate disinfectants or a salt thereof.

In an embodiment, the composition of the invention comprises:

(a) ethoxyethyl methacrylate as one or more film forming agents; and (b) one or more $(C_1-C_6)$alkyl N(alpha)-$(C_{10}-C_{25})$alkanoyl-L-arginate disinfectants or a salt thereof.

In an embodiment, the composition of the invention comprises:

(a) 2-ethoxyethyl methacrylate as one or more film forming agents; and (b) $(C_1-C_6)$alkyl lauroyl arginate or a salt thereof as a disinfectant.

In an embodiment, the composition of the invention comprises:

(a) 2-ethoxyethyl methacrylate as one or more film forming agents; and (b) ethyl lauroyl arginate or a salt thereof as a disinfectant; particularly hydrochloride salt.

In an embodiment, the composition comprises chlorhexidine or a salt thereof as a disinfectant (b). In an embodiment, the composition comprises chlorhexidine as a disinfectant (b). In an embodiment, the composition comprises a salt of chlorhexidine as a disinfectant (b). In an embodiment, the composition comprises chlorhexidine digluconate as a disinfectant (b).

In an embodiment, the composition of the invention comprises:

(a) one or more film forming $(C_1-C_6)$alkoxy $(C_1-C_6)$ alkyl methacrylate polymers; and (b) chlorhexidine as a disinfectant or a salt thereof.

In an embodiment, the composition of the invention comprises:

(a) 2-ethoxyethyl methacrylate as one or more film forming agents; and (b) chlorhexidine as a disinfectant or a salt thereof.

In an embodiment, the composition of the invention comprises:

(a) 2-ethoxyethyl methacrylate as one or more film forming agents; and (b) chlorhexidine digluconate as a disinfectant.

In an embodiment, the composition of the invention comprises:

(a) from 5 to 20% by weight in relation to the weight of the composition of one or more film formings as defined herein; and (b) from 0.02 to 0.40% by weight in relation to the weight of the composition of one or more disinfectants as defined herein.

In an embodiment, the composition of the invention comprises:

(a) from 5 to 20% by weight in relation to the weight of the composition of one or more film forming $(C_1-C_6)$ alkoxy $(C_1-C_6)$ alkyl methacrylate polymers, particularly 2-ethoxyethyl methacrylate; and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof.

In an embodiment, the composition of the invention comprises:

(a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film forming $(C_1-C_6)$ alkoxy $(C_1-C_6)$ alkyl methacrylate polymers, particularly 2-ethoxyethyl methacrylate; and (b) from 0.02 to 0.40% by weight in relation to the weight of the composition of chlorhexidine as definfectant or a salt thereof.

In an embodiment, the composition of the invention comprises:

(a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of chlorhexidine as definfectant or a salt thereof; particularly chlorhexidine digluconate.

As it is mentioned above, the composition of the first aspect of the invention comprises a "solvent system" that comprises: (c1) one or more water immiscible solvents selected from the group consisting of $(C_1-C_5)$alkyl-CO—O—$(C_1-C_6)$alkyl, $((C_1-C_6)$alkyl$)_3$Si—O—Si$((C_1-C_6)$ alkyl$)_3$, $(C_1-C_5)$alkyl-O—$(C_2-C_5)$alkyl and a mixture thereof; (c2) acetone; (c3) one or more $(C_2-C_3)$ alcohols; and optionally (c4) as defined below. For the purpose of the invention the term "solvent system" is the mixture of the solvents that comprises at least one of (c1), acetone (c2) and one of (c3); and optionally (c4) as defined below.

In an embodiment, the composition comprises one or more water immiscible solvents selected from the group consisting of $(C_1-C_6)$alkyl-CO—O—$(C_1-C_6)$alkyl, $((C_1-C_6)$ alkyl$)_3$Si—O—Si$((C_1-C_6)$alkyl$)_3$, $(C_1-C_5)$alkyl-O—$(C_2-C_5)$ alkyl and a mixture thereof. The term "immiscible solvent" refers to any solvent that, when combined, form two phases, which means that the mixture thus obtained is "biphasic" under specified conditions of component concentrations and temperature, among others. Further, the term "water-immiscible solvent" refers to any solvent that can form a biphasic phase with water at the temperature at which the reaction is carried out. As used herein, the term "biphasic" refers to a reaction medium that includes two immiscible liquid phases, for example, an aqueous phase and a water-immiscible solvent phase. The term "biphasic" can also be used to describe a method employing such a reaction medium. In an embodiment, the composition comprises one or more $(C_1$-$C_5)$alkyl-CO—O—$(C_1$-$C_6)$alkyl as water immiscible solvents (c1). In an embodiment, the composition comprises one or more $(C_1$-$C_5)$alkyl-CO—O—$(C_1$-$C_6)$alkyl as water immiscible solvents (c1) selected from the group consisting of ethyl acetate, isopropyl acetate, n-propyl acetate, and a mixture thereof. In an embodiment, the composition comprises ethyl acetate as the $(C_1$-$C_5)$alkyl-CO—O—$(C_1$-$C_6)$ alkyl (c1). In an embodiment, the composition comprises one or more $(C_1$-$C_6)$alkyl$)_3$Si—O—Si$((C_1$-$C_6)$alkyl$)_3$ as water immiscible solvents (c1). In an embodiment, the composition comprises one or more $(C_1$-$C_6)$alkyl$)_3$Si—O—Si$((C_1$-$C_6)$alkyl$)_3$ as water immiscible solvents (c1) comprising hexamethyldisiloxane. In an embodiment, the composition comprises hexamethyldisiloxane as one or more $(C_1$-$C_6)$alkyl$)_3$Si—O—Si$((C_1$-$C_6)$alkyl$)_3$ as water immiscible solvents (c1). In an embodiment, the composition comprises a mixture of one or more $(C_1$-$C_5)$alkyl-CO—O—$(C_1$-$C_6)$alkyl and one or more $(C_1$-$C_6)$alkyl$)_3$Si—O—Si$((C_1$-$C_6)$alkyl$)_3$ as defined above as water immiscible solvents (c1). In an embodiment, the composition comprises a mixture of one $(C_1$-$C_5)$alkyl-CO—O—$(C_1$-$C_6)$alkyl and one $(C_1$-$C_6)$alkyl$)_3$Si—O—Si$((C_1$-$C_6)$alkyl$)_3$ as water immiscible solvents (c1). In an embodiment, the composition comprises a mixture of ethylacetate and hexamethyldililoxane as water immiscible solvents (c1). In an embodiment, the composition comprises one or more $(C_1$-$C_5)$alkyl-O—$(C_2$-$C_5)$alkyl as water immiscible solvents (c1). In an embodiment, the composition comprises one or more $(C_1$-$C_5)$alkyl-O—$(C_2$-$C_5)$alkyl as water immiscible solvents (c1) selected from the group consisting of diethylether, diisopropylether, tert-butyl methyl ether and a mixture thereof; particularly tert-butyl methyl ether.

In an embodiment, the composition comprises one or more $(C_2$-$C_3)$ alcohols (c3) selected from the group consisting of ethanol, n-propanol, iso-propanol, and a mixture thereof. In an embodiment, the composition comprises a mixture of ethanol and isopropanol as $(C_2$-$C_3)$ alcohols (c3). And the term "alcohol" refers to an "alkane" wherein at least one hydrogen atom is substituted by a hydroxyl group and which contains the number of carbon atoms specified in the description or claims. The term "alkane" refers to a saturated, branched, or linear hydrocarbon which contains the number of carbon atoms specified in the description or claims. Examples include ethanol, n-propanol, and iso-propanol.

In an embodiment, the composition comprises a solvent system comprising:
- (c1) water immiscible solvents (c1) selected from the group consisting of $(C_1$-$C_5)$alkyl-CO—O—$(C_1$-$C_6)$alkyl, $((C_1$-$C_6)$alkyl$)_3$Si—O—Si$((C_1$-$C_6)$alkyl$)_3$, and a mixture thereof:
- (c2) acetone; and
- (c3) one or more $(C_2$-$C_3)$ alcohols; particularly ethanol, isopropanol and a mixture thereof.

In an embodiment, the composition comprises a solvent system comprising:
- (c1) one or more of $(C_1$-$C_5)$alkyl-CO—O—$(C_1$-$C_6)$alkyl as water immiscible solvents;
- (c2) acetone; and

- (c3) a mixture of ethanol and isopropanol as $(C_2$-$C_3)$ alcohols.

In an embodiment, the composition comprises a solvent system comprising:
- (c1) ethylacetate as $(C_1$-$C_5)$alkyl-CO—O—$(C_1$-$C_6)$alkyl water immiscible solvents;
- (c2) acetone; and
- (c3) a mixture of ethanol and isopropanol as $(C_2$-$C_3)$ alcohols.

In an embodiment, the composition comprises a solvent system comprising:
- (c1) a mixture of one or more of $(C_1$-$C_5)$alkyl-CO—O—$(C_1$-$C_6)$alkyl and $((C_1$-$C_6)$alkyl$)_3$Si—O—Si$((C_1$-$C_6)$alkyl$)_3$ as water immiscible solvents;
- (c2) acetone; and
- (c3) a mixture of ethanol and isopropanol as $(C_2$-$C_3)$ alcohols.

In an embodiment, the composition comprises a solvent system comprising:
- (c1) a mixture of ethyl acetate and hexamethyldisiloxane as water immiscible solvents;
- (c2) acetone; and
- (c3) one or more $(C_2$-$C_3)$ alcohols; particularly ethanol, isopropanol and a mixture thereof; particularly isopropanol.

In an embodiment, the "solvent system" of the composition further comprises: (c4) one or more water-miscible solvents. The term "miscible solvent" refers to any solvent that, when combined, form a single phase, which means that the mixture thus obtained is "monophasic" under specified conditions of component concentrations and temperature among others. Further, the term "water-miscible solvent" refers to any solvent that can form a monophasic solution with water at the temperature at which the reaction is carried out. As used herein, the term "monophasic" refers to a reaction medium that includes only one liquid phase, and also a method employing such a reaction medium. Some examples of monophasic mediums are water, aqueous solutions, and solutions containing aqueous and organic solvents that are miscible with each other. In an embodiment, the "solvent system" of the composition further comprises: (c4) one or more water-miscible solvents selected from the group consisting of water, glycol, glycerine and a mixture thereof. In an embodiment, the "solvent system" of the composition further comprises water as (c4). In an embodiment, the "solvent system" of the composition further comprises one or more glycols (c4); particularly selected from ethilenglycol and propylen glycol. In an embodiment, the "solvent system" of the composition further comprises: a mixture of water and one or more glycols as (c4). The term "glycol" refers to any organic compound containing two hydroxyl (OH) groups bound to different carbon atoms, usually but not necessary adyacents. For the purpose of the present invention, the term glycol refers to HO—$(C_1$-$C_6)$Alkyl-OH and OH—$(C_1$-$C_6)$Alkyl-O—$(C_1$-$C_6)$Alkyl-OH.

In an embodiment, the composition comprises a solvent system comprising:
- (c1) water immiscible solvents (c1) selected from the group consisting of $(C_1$-$C_5)$alkyl-CO—O—$(C_1$-$C_6)$alkyl, $((C_1$-$C_6)$alkyl$)_3$Si—O—Si$((C_1$-$C_6)$alkyl$)_3$, and a mixture thereof:
- (c2) acetone;
- (c3) one or more $(C_2$-$C_3)$ alcohols; particularly ethanol, isopropanol and a mixture thereof; and
- (c4) one or more water-miscible solvents selected from the group consisting of water, glycol, glycerine and a mixture thereof.

In an embodiment, the composition comprises a solvent system comprising:

(c1) water immiscible solvents (c1) selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, and a mixture thereof;

(c2) acetone;

(c3) one or more $(C_2-C_3)$ alcohols; particularly ethanol, isopropanol and a mixture thereof; and (c4) a mixture of water and glycerine as water-miscible solvents.

In an embodiment, the composition comprises a solvent system comprising:

(c1) one or more of $(C_1-C_5)$alkyl-CO—O—$(C_1-C_6)$alkyl as water immiscible solvents;

(c2) acetone;

(c3) a mixture of ethanol and isopropanol as $(C_2-C_3)$ alcohols; and (c4) one or more water-miscible solvents selected from the group consisting of water, glycol, glycerine and a mixture thereof.

In an embodiment, the composition comprises a solvent system comprising:

(c1) one or more of $(C_1-C_5)$alkyl-CO—O—$(C_1-C_6)$alkyl as water immiscible solvents;

(c2) acetone;

(c3) a mixture of ethanol and isopropanol as $(C_2-C_3)$ alcohols; and (c4) a mixture of water and glycerine as water-miscible solvents.

In an embodiment, the composition comprises a solvent system comprising:

(c1) ethylacetate as $(C_1-C_5)$alkyl-CO—O—$(C_1-C_6)$alkyl water immiscible solvents;

(c2) acetone;

(c3) a mixture of ethanol and isopropanol as $(C_2-C_3)$ alcohols; and (c4) one or more water-miscible solvents selected from the group consisting of water, glycol, glycerine and a mixture thereof.

In an embodiment, the composition comprises a solvent system comprising:

(c1) ethylacetate as $(C_1-C_5)$alkyl-CO—O—$(C_1-C_6)$alkyl water immiscible solvents;

(c2) acetone;

(c3) a mixture of ethanol and isopropanol as $(C_2-C_3)$ alcohols; and (c4) a mixture of water and glycerine as water-miscible solvents.

In an embodiment, the composition comprises a solvent system comprising:

(c1) a mixture of one or more of $(C_1-C_5)$alkyl-CO—O—$(C_1-C_6)$alkyl and $((C_1-C_6)$alkyl$)_3$Si—O—Si$((C_1-C_6)$alkyl$)_3$ as water immiscible solvents;

(c2) acetone;

(c3) a mixture of ethanol and isopropanol as $(C_2-C_3)$ alcohols; and (c4) one or more water-miscible solvents selected from the group consisting of water, glycol, glycerine and a mixture thereof.

In an embodiment, the composition comprises a solvent system comprising:

(c1) a mixture of one or more of $(C_1-C_5)$alkyl-CO—O—$(C_1-C_6)$alkyl and $((C_1-C_6)$alkyl$)_3$Si—O—Si$((C_1-C_6)$alkyl$)_3$ as water immiscible solvents;

(c2) acetone;

(c3) a mixture of ethanol and isopropanol as $(C_2-C_3)$ alcohols; and (c4) a mixture of water and glycerine as water-miscible solvents.

In an embodiment, the composition comprises a solvent system comprising:

(c1) a mixture of ethyl acetate and hexamethyldisiloxane as water immiscible solvents;

(c2) acetone;

(c3) one or more $(C_2-C_3)$ alcohols; particularly ethanol, isopropanol and a mixture thereof; particularly isopropanol; and (c4) one or more water-miscible solvents selected from the group consisting of water, glycol, glycerine and a mixture thereof.

In an embodiment, the composition comprises a solvent system comprising:

(c1) a mixture of ethyl acetate and hexamethyldisiloxane as water immiscible solvents;

(c2) acetone;

(c3) one or more $(C_2-C_3)$ alcohols; particularly ethanol, isopropanol and a mixture thereof; particularly isopropanol; and (c4) a mixture of water and glycerine as water-miscible solvents.

In an embodiment, the composition of the invention comprises: (c) from 80 to 95% by weight of a solvent system in relation to the total weight of the composition.

In an embodiment, the composition of the invention comprises:

(c) from 80 to 95% by weight of a solvent system comprising:

(c1) from 1 to 25% by weight in relation to the total weight of the solvent system of the water-immiscible solvents as defined above;

(c2) from 1 to 70% by weight in relation to the total weight of the solvent system of acetone;

(c3) from 5 to 70% by weight in relation to the total weight of the solvent system of $(C_2-C_3)$ alcohols as defined above;

(c4) from 0 to 20% by weight in relation to the total weight of the solvent system of one or more water-miscible solvent selected from water, glycol, and a mixture thereof;

being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of one or more water immiscible solvents (c1) selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, and a mixture thereof;

(c2) from 1 to 70% by weight in relation to the total weight of the solvent system acetone;

(c3) from 5 to 70% by weight in relation to the total weight of the solvent system of one or more $(C_2-C_3)$ alcohols; particularly ethanol, isopropanol and a mixture thereof; and (c4) from 0 to 20% by weight in relation to the total weight of the solvent system one or more water-miscible solvents selected from the group consisting of water, glycol, glycerine and a mixture thereof; being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of one or more water immiscible solvents (c1) selected from the group consisting of $(C_1-C_5)alkyl-CO-O-(C_1-C_6)alkyl$, $((C_1-C_6)alkyl)_3Si-O-Si((C_1-C_6)alkyl)_3$, and a mixture thereof:

(c2) from 1 to 70% by weight in relation to the total weight of the solvent system of acetone;

(c3) from 5 to 70% by weight in relation to the total weight of the solvent system of one or more $(C_2-C_3)$ alcohols; particularly ethanol, isopropanol and a mixture thereof; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of one or more of $(C_1-C_5)alkyl-CO-O-(C_1-C_6)alkyl$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of one or more of $(C_1-C_5)alkyl-CO-O-(C_1-C_6)alkyl$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of ethylacetate as $(C_1-C_5)$ alkyl-CO-O-$(C_1-C_6)$alkyl water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of ethylacetate as $(C_1-C_5)$ alkyl-CO-O-$(C_1-C_6)$alkyl water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of a mixture of one or more of $(C_1-C_5)alkyl-CO-O-(C_1-C_6)alkyl$ and $((C_1-C_6)alkyl)_3Si-O-Si((C_1-C_6)alkyl)_3$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of a mixture of one or more of $(C_1-C_5)alkyl-CO-O-(C_1-C_6)alkyl$ and $((C_1-C_6)alkyl)_3Si-O-Si((C_1-C_6)alkyl)_3$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of a mixture of ethyl acetate and hexamethyldisiloxane as water immiscible solvents;

(c2) from 1 to 70% by weight in relation to the total weight of the solvent system of acetone;

(c3) from 5 to 70% by weight in relation to the total weight of the solvent system of one or more $(C_2\text{-}C_3)$ alcohols; particularly ethanol, isopropanol and a mixture thereof; particularly isopropanol; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system.

In an embodiment, the composition comprises a solvent system comprising:

(c1) from 1 to 25% by weight in relation to the total weight of the solvent system of a mixture of ethyl acetate and hexamethyldisiloxane as water immiscible solvents;

(c2) from 1 to 70% by weight in relation to the total weight of the solvent system of acetone;

(c3) from 5 to 70% by weight in relation to the total weight of the solvent system of one or more $(C_2\text{-}C_3)$ alcohols; particularly ethanol, isopropanol and a mixture thereof; particularly isopropanol; and (c4) from 0 to 20% by weight in relation to the total weight of the solvent system of a mixture of water and glycerine as water-miscible solvents in relation to the total weight of the solvent system; being the sum of (c1), (c2), (c3) and (c4) up to 100% by weight in relation to the total weight of the solvent system.

In an embodiment, the composition comprises:

(a) one or more film forming $(C_1\text{-}C_6)$alkoxy $(C_1\text{-}C_6)$ alkyl methacrylate polymers; and (b) one or more $(C_1\text{-}C_6)$alkyl N(alpha)-$(C_{10}\text{-}C_{25})$alkanoyl-L-arginate disinfectants or a salt thereof;

(c) a solvent system comprising:

(c1) water immiscible solvents (c1) selected from the group consisting of $(C_1\text{-}C_5)$alkyl-CO—O—$(C_1\text{-}C_6)$alkyl, $((C_1\text{-}C_6)$alkyl$)_3$Si—O—Si$((C_1\text{-}C_6)$alkyl$)_3$, and a mixture thereof:

(c2) acetone;

(c3) one or more $(C_2\text{-}C_3)$ alcohols; particularly ethanol, isopropanol and a mixture thereof; and (c4) optionally, one or more water-miscible solvents selected from the group consisting of water, glycol, glycerine and a mixture thereof;

particularly, (a) 2-ethoxyethyl methacrylate as one or more film forming agents; and (b) $(C_1\text{-}C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1\text{-}C_6)$alkoxy $(C_1\text{-}C_6)$ alkyl methacrylate polymers; and (b) one or more $(C_1\text{-}C_6)$alkyl N(alpha)-$(C_{10}\text{-}C_{25})$alkanoyl-L-arginate disinfectants or a salt thereof;

(c) a solvent system comprising:

(c1) one or more of $(C_1\text{-}C_5)$alkyl-CO—O—$(C_1\text{-}C_6)$alkyl as water immiscible solvents;

(c2) acetone;

(c3) a mixture of ethanol and isopropanol as $(C_2\text{-}C_3)$ alcohols; and (c4) optionally, one or more water-miscible solvents selected from the group consisting of water, glycol, glycerine and a mixture thereof;

particularly, (a) 2-ethoxyethyl methacrylate as one or more film forming agents; and (b) $(C_1\text{-}C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1\text{-}C_6)$alkoxy $(C_1\text{-}C_6)$ alkyl methacrylate polymers; and (b) one or more $(C_1\text{-}C_6)$alkyl N(alpha)-$(C_{10}\text{-}C_{25})$alkanoyl-L-arginate disinfectants or a salt thereof;

(c) a solvent system comprising:

(c1) one or more of $(C_1\text{-}C_5)$alkyl-CO—O—$(C_1\text{-}C_6)$alkyl as water immiscible solvents;

(c2) acetone;

(c3) a mixture of ethanol and isopropanol as $(C_2\text{-}C_3)$ alcohols; and (c4) optionally, a mixture of water and glycerine as water-miscible solvents;

particularly, (a) 2-ethoxyethyl methacrylate as one or more film forming agents; and (b) $(C_1\text{-}C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1\text{-}C_6)$alkoxy $(C_1\text{-}C_6)$ alkyl methacrylate polymers; and (b) one or more $(C_1-C_6)$alkyl N(alpha)-$(C_{10}-C_{25})$alkanoyl-L-arginate disinfectants or a salt thereof;

(c) a solvent system comprising:

(c1) ethylacetate as $(C_1-C_5)$alkyl-CO—O—$(C_1-C_6)$alkyl water immiscible solvents;

(c2) acetone;

(c3) a mixture of ethanol and isopropanol as $(C_2-C_3)$ alcohols; and (c4) one or more water-miscible solvents selected from the group consisting of water, glycol, glycerine and a mixture thereof.

In an embodiment, the composition comprises:

(a) one or more film forming $(C_1-C_6)$alkoxy $(C_1-C_6)$ alkyl methacrylate polymers; and (b) chlorhexidine as disinfectant or a salt thereof;

(c) a solvent system comprising:

(c1) water immiscible solvents (c1) selected from the group consisting of $(C_1-C_5)$alkyl-CO—O—$(C_1-C_6)$alkyl, $((C_1-C_6)alkyl)_3Si—O—Si((C_1-C_6)alkyl)_3$, and a mixture thereof:

(c2) acetone;

(c3) one or more $(C_2-C_3)$ alcohols; particularly ethanol, isopropanol and a mixture thereof; and (c4) optionally, one or more water-miscible solvents selected from the group consisting of water, glycol, glycerine and a mixture thereof;

particularly, (a) 2-ethoxyethyl methacrylate as one or more film forming agents; and (b) chlorhexidine or a salt thereof as a disinfectant; or (a) 2-ethoxyethyl methacrylate as one or more film forming agents; and (b) chlorhexidine digluconate as disinfectant.

In an embodiment, the composition comprises:

(a) one or more film forming $(C_1-C_6)$alkoxy $(C_1-C_6)$ alkyl methacrylate polymers; and (b) chlorhexidine as disinfectant or a salt thereof;

(c) a solvent system comprising:

(c1) water immiscible solvents (c1) selected from the group consisting of $(C_1-C_5)$alkyl-CO—O—$(C_1-C_6)$alkyl, $((C_1-C_6)alkyl)_3Si—O—Si((C_1-C_6)alkyl)_3$, and a mixture thereof:

(c2) acetone;

(c3) one or more $(C_2-C_3)$ alcohols; particularly ethanol, isopropanol and a mixture thereof; and (c4) optionally, a mixture of water and glycerine as water-miscible solvents;

particularly, (a) 2-ethoxyethyl methacrylate as one or more film forming agents; and (b) chlorhexidine or a salt thereof as disinfectant; or (a) 2-ethoxyethyl methacrylate as one or more film forming agents; and (b) chlorhexidine digluconate as disinfectant.

In an embodiment, the composition comprises:

(a) one or more film forming $(C_1-C_6)$alkoxy $(C_1-C_6)$ alkyl methacrylate polymers; and (b) chlorhexidine as disinfectant or a salt thereof;

(c) a solvent system comprising:

(c1) one or more of $(C_1-C_5)$alkyl-CO—O—$(C_1-C_6)$alkyl as water immiscible solvents;

(c2) acetone;

(c3) a mixture of ethanol and isopropanol as $(C_2-C_3)$ alcohols; and (c4) optionally, one or more water-miscible solvents selected from the group consisting of water, glycol, glycerine and a mixture thereof;

particularly, (a) 2-ethoxyethyl methacrylate as one or more film forming agents; and (b) chlorhexidine or a salt thereof as disinfectant; or (a) 2-ethoxyethyl methacrylate as one or more film forming agents; and (b) chlorhexidine digluconate as disinfectant.

In an embodiment, the composition comprises:

(a) one or more film forming $(C_1-C_6)$alkoxy $(C_1-C_6)$ alkyl methacrylate polymers; and (b) chlorhexidine as disinfectant or a salt thereof;

(c) a solvent system comprising:

(c1) one or more of $(C_1-C_5)$alkyl-CO—O—$(C_1-C_6)$alkyl as water immiscible solvents;

(c2) acetone;

(c3) a mixture of ethanol and isopropanol as $(C_2-C_3)$ alcohols; and (c4) optionally, a mixture of water and glycerine as water-miscible solvents;

particularly, (a) 2-ethoxyethyl methacrylate as one or more film forming agents; and (b) chlorhexidine as disinfectant; or (a) 2-ethoxyethyl methacrylate as one or more film forming agents; and (b) chlorhexidine digluconate as disinfectant.

In an embodiment, the composition comprises:

(a) one or more film forming $(C_1-C_6)$alkoxy $(C_1-C_6)$ alkyl methacrylate polymers; and (b) chlorhexidine as disinfectant or a salt thereof;

(c) a solvent system comprising:

(c1) ethylacetate as $(C_1-C_5)$alkyl-CO—O—$(C_1-C_6)$alkyl water immiscible solvents;

(c2) acetone;

(c3) a mixture of ethanol and isopropanol as $(C_2-C_3)$ alcohols; and (c4) one or more water-miscible solvents selected from the group consisting of water, glycol, glycerine and a mixture thereof.

In an embodiment, the composition comprises a solvent system comprising:

(c1) ethylacetate as $(C_1-C_5)$alkyl-CO—O—$(C_1-C_6)$alkyl water immiscible solvents;

(c2) acetone;

(c3) a mixture of ethanol and isopropanol as $(C_2-C_3)$ alcohols; and (c4) optionally, a mixture of water and glycerine as water-miscible solvents;

particularly, (a) 2-ethoxyethyl methacrylate as one or more film forming agents; and (b) $(C_1-C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1-C_6)$alkoxy $(C_1-C_6)$ alkyl methacrylate polymers; and (b) one or more $(C_1-C_6)$alkyl N(alpha)-$(C_{10}-C_{25})$alkanoyl-L-arginate disinfectants or a salt thereof;

(c) a solvent system comprising:

(c1) a mixture of one or more of $(C_1-C_5)$alkyl-CO—O—$(C_1-C_6)$alkyl and $((C_1-C_6)alkyl)_3Si—O—Si((C_1-C_6)alkyl)_3$ as water immiscible solvents;

(c2) acetone;

(c3) a mixture of ethanol and isopropanol as $(C_2-C_3)$ alcohols; and (c4) optionally, one or more water-miscible solvents selected from the group consisting of water, glycol, glycerine and a mixture thereof;

particularly, (a) 2-ethoxyethyl methacrylate as one or more film forming agents; and (b) $(C_1-C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1-C_6)$alkoxy $(C_1-C_6)$ alkyl methacrylate polymers; and (b) one or more $(C_1-C_6)$alkyl N(alpha)-$(C_{10}-C_{25})$alkanoyl-L-arginate disinfectants or a salt thereof;

(c) a solvent system comprising:

(c1) a mixture of one or more of $(C_1-C_5)$alkyl-CO—O—$(C_1-C_6)$alkyl and $((C_1-C_6)$alkyl$)_3$Si—O—Si$((C_1-C_6)$ alkyl$)_3$ as water immiscible solvents;

(c2) acetone;

(c3) a mixture of ethanol and isopropanol as $(C_2-C_3)$ alcohols; and (c4) optionally, a mixture of water and glycerine as water-miscible solvents;

particularly, (a) 2-ethoxyethyl methacrylate as one or more film forming agents; and (b) $(C_1-C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1-C_6)$alkoxy $(C_1-C_6)$ alkyl methacrylate polymers; and (b) one or more $(C_1-C_6)$alkyl N(alpha)-$(C_{10}-C_{25})$alkanoyl-L-arginate disinfectants or a salt thereof;

(c) a solvent system comprising:

(c1) a mixture of ethyl acetate and hexamethyldisiloxane as water immiscible solvents;

(c2) acetone;

(c3) one or more $(C_2-C_3)$ alcohols; particularly ethanol, isopropanol and a mixture thereof; particularly isopropanol; and (c4) optionally, one or more water-miscible solvents selected from the group consisting of water, glycol, glycerine and a mixture thereof;

particularly, (a) 2-ethoxyethyl methacrylate as one or more film forming agents; and (b) $(C_1-C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) one or more film forming $(C_1-C_6)$alkoxy $(C_1-C_6)$ alkyl methacrylate polymers; and (b) one or more $(C_1-C_6)$alkyl N(alpha)-$(C_{10}-C_{25})$alkanoyl-L-arginate disinfectants or a salt thereof;

(c) a solvent system comprising:

(c1) a mixture of ethyl acetate and hexamethyldisiloxane as water immiscible solvents;

(c2) acetone;

(c3) one or more $(C_2-C_3)$ alcohols; particularly ethanol, isopropanol and a mixture thereof; particularly isopropanol; and (c4) optionally, a mixture of water and glycerine as water-miscible solvents;

particularly, (a) 2-ethoxyethyl methacrylate as one or more film forming agents; and (b) $(C_1-C_6)$alkyl lauroyl arginate or a salt thereof as a disinfectant; or (a) 2-ethoxyethyl methacrylate as one or more film forming agents; and (b) ethyl lauroyl arginate or a salt thereof as a disinfectant; particularly hydrochloride salt.

In an embodiment, the composition comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of the water-immiscible solvents as defined above;

(c2) from 1 to 70% by weight in relation to the total weight of the solvent system of acetone;

(c3) from 5 to 70% by weight in relation to the total weight of the solvent system of $(C_2-C_3)$ alcohols as defined above;

(c4) from 0 to 20% by weight in relation to the total weight of the solvent system of one or more water-miscible solvent selected from water, glycol, and a mixture thereof;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of one or more water immiscible solvents (c1) selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, and a mixture thereof:

(c2) from 1 to 70% by weight in relation to the total weight of the solvent system acetone;

(c3) from 5 to 70% by weight in relation to the total weight of the solvent system of one or more $(C_2-C_3)$ alcohols; particularly ethanol, isopropanol and a mixture thereof; and (c4) from 0 to 20% by weight in relation to the total weight of the solvent system one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of one or more water immiscible solvents (c1) selected from the group consisting of $(C_1-C_5)$alkyl-CO—O—$(C_1-C_6)$alkyl, $((C_1-C_6)$alkyl$)_3$Si—O—Si$((C_1-C_6)$alkyl$)_3$, and a mixture thereof:

(c2) from 1 to 70% by weight in relation to the total weight of the solvent system of acetone;

(c3) from 5 to 70% by weight in relation to the total weight of the solvent system of one or more $(C_2-C_3)$ alcohols; particularly ethanol, isopropanol and a mixture thereof; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of one or more of $(C_1-C_5)$alkyl-CO—O—$(C_1-C_6)$alkyl as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of one or more of $(C_1-C_5)$alkyl-CO—O—$(C_1-C_6)$alkyl as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of ethylacetate as $(C_1-C_5)$ alkyl-CO—O—$(C_1-C_6)$alkyl water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of ethylacetate as $(C_1-C_5)$ alkyl-CO—O—$(C_1-C_6)$alkyl water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of a mixture of one or more of $(C_1-C_5)$alkyl-CO—O—$(C_1-C_6)$alkyl and $((C_1-C_6)$alkyl$)_3$Si—O—Si$((C_1-C_6)$alkyl$)_3$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of a mixture of one or more of $(C_1-C_5)$alkyl-CO—O—$(C_1-C_6)$alkyl and $((C_1-C_6)$alkyl$)_3$Si—O—Si$((C_1-C_6)$alkyl$)_3$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2-C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1-C_6)$ alkoxy $(C_1-C_6)$ alkyl methacrylate polymers: and (b) from 0.02 to 0.40% by weight in relation to the weight of the composition of one or more $(C_1-C_6)$alkyl N(alpha)-$(C_{10}-C_{25})$alkanoyl-L-arginate disinfectants or a salt thereof;

or (a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of 2-ethoxyethyl methacrylate as $(C_1-C_6)$alkoxy $(C_1-C_6)$ alkyl methacrylate film forming polymer; and (b) from 0.02 to 0.40% by weight in relation to the weight of the composition of ethyl lauroyl arginate or a salt thereof as $(C_1-C_6)$alkyl N(alpha)-$(C_{10}-C_{25})$alkanoyl-L-arginate disinfectant; particularly hydrochloride salt.

In an embodiment, the composition of the invention comprises:

(a) from 5 to 20% by weight in relation to the weight of the composition of one or more film formings;

(b) from 0.02 to 0.40% by weight in relation to the weight of the composition of one or more disinfectants; and (c) from 80 to 95% by weight of a solvent system comprising:

(c1) from 1 to 25% by weight in relation to the total weight of the solvent system of a mixture of ethyl acetate and hexamethyldisiloxane as water immiscible solvents;

(c2) from 1 to 70% by weight in relation to the total weight of the solvent system of acetone;

(c3) from 5 to 70% by weight in relation to the total weight of the solvent system of one or more $(C_2\text{-}C_3)$ alcohols; particularly ethanol, isopropanol and a mixture thereof; particularly isopropanol; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of one or more film forming $(C_1\text{-}C_6)$ alkoxy $(C_1\text{-}C_6)$ alkyl methacrylate polymers; and (b) from 0.02 to 0.40% by weight in relation to the weight of the composition of one or more $(C_1\text{-}C_6)$alkyl N(alpha)-$(C_{10}\text{-}C_{25})$alkanoyl-L-arginate disinfectants or a salt thereof;

or (a) from 5 to 20% by weight in relation to the weight of the composition of 2-ethoxyethyl methacrylate as $(C_1\text{-}C_6)$alkoxy $(C_1\text{-}C_6)$ alkyl methacrylate film forming polymer; and (b) from 0.02 to 0.40% by weight in relation to the weight of the composition of ethyl lauroyl arginate or a salt thereof as $(C_1\text{-}C_6)$alkyl N(alpha)-$(C_{10}\text{-}C_{25})$alkanoyl-L-arginate disinfectant; particularly hydrochloride salt.

In an embodiment, the composition comprises a solvent system comprising:

(c1) ethylacetate as $(C_1\text{-}C_5)$alkyl-CO—O—$(C_1\text{-}C_6)$alkyl water immiscible solvents;

(c2) acetone;

(c3) a mixture of ethanol and isopropanol as $(C_2\text{-}C_3)$ alcohols; and (c4) optionally, a mixture of water and glycerine as water-miscible solvents;

particularly, (a) 2-ethoxyethyl methacrylate as one or more film forming agents; and (b) chlorhexidine or a salt thereof as a disinfectant; or (a) 2-ethoxyethyl methacrylate as one or more film forming agents; and (b) chlorhexidine digluconate as a disinfectant.

In an embodiment, the composition comprises:

(a) one or more film forming $(C_1\text{-}C_6)$alkoxy $(C_1\text{-}C_6)$ alkyl methacrylate polymers; and (b) chlorhexidine as disinfectant or a salt thereof;

(c) a solvent system comprising:

(c1) a mixture of one or more of $(C_1\text{-}C_5)$alkyl-CO—O—$(C_1\text{-}C_6)$alkyl and $((C_1\text{-}C_6)$alkyl)$_3$Si—O—Si($(C_1\text{-}C_6)$ alkyl)$_3$ as water immiscible solvents;

(c2) acetone;

(c3) a mixture of ethanol and isopropanol as $(C_2\text{-}C_3)$ alcohols; and (c4) optionally, one or more water-miscible solvents selected from the group consisting of water, glycol, glycerine and a mixture thereof;

particularly, (a) 2-ethoxyethyl methacrylate as one or more film forming agents; and (b) chlorhexidine or a salt thereof as a disinfectant; or (a) 2-ethoxyethyl methacrylate as one or more film forming agents; and (b) chlorhexidine digluconate as a disinfectant.

In an embodiment, the composition comprises:

(a) one or more film forming $(C_1\text{-}C_6)$alkoxy $(C_1\text{-}C_6)$ alkyl methacrylate polymers; and (b) chlorhexidine or a salt thereof as a disinfectant;

(c) a solvent system comprising:

(c1) a mixture of one or more of $(C_1\text{-}C_5)$alkyl-CO—O—$(C_1\text{-}C_6)$alkyl and $((C_1\text{-}C_6)$alkyl)$_3$Si—O—Si($(C_1\text{-}C_6)$ alkyl)s as water immiscible solvents;

(c2) acetone;

(c3) a mixture of ethanol and isopropanol as $(C_2\text{-}C_3)$ alcohols; and (c4) optionally, a mixture of water and glycerine as water-miscible solvents;

particularly, (a) 2-ethoxyethyl methacrylate as one or more film forming agents; and (b) chlorhexidine or a salt thereof as a disinfectant; or (a) 2-ethoxyethyl methacrylate as one or more film forming agents; and (b) chlorhexidine digluconate as a disinfectant.

In an embodiment, the composition comprises:

(a) one or more film forming $(C_1\text{-}C_6)$alkoxy $(C_1\text{-}C_6)$ alkyl methacrylate polymers; and (b) chlorhexidine or a salt thereof as a disinfectant;

(c) a solvent system comprising:

(c1) a mixture of ethyl acetate and hexamethyldisiloxane as water immiscible solvents;

(c2) acetone;

(c3) one or more $(C_2\text{-}C_3)$ alcohols; particularly ethanol, isopropanol and a mixture thereof; particularly isopropanol; and (c4) optionally, one or more water-miscible solvents selected from the group consisting of water, glycol, glycerine and a mixture thereof;

particularly, (a) 2-ethoxyethyl methacrylate as one or more film forming agents; and (b) chlorhexidine or a salt thereof as a disinfectant or (a) 2-ethoxyethyl methacrylate as one or more film forming agents; and (b) chlorhexidine digluconate as a disinfectant.

In an embodiment, the composition comprises:

(a) one or more film forming $(C_1\text{-}C_6)$alkoxy $(C_1\text{-}C_6)$ alkyl methacrylate polymers; and (b) chlorhexidine or a salt thereof as a disinfectant;

(c) a solvent system comprising:

(c1) a mixture of ethyl acetate and hexamethyldisiloxane as water immiscible solvents;

(c2) acetone;

(c3) one or more $(C_2\text{-}C_3)$ alcohols; particularly ethanol, isopropanol and a mixture thereof; particularly isopropanol; and (c4) optionally, a mixture of water and glycerine as water-miscible solvents;

particularly, (a) 2-ethoxyethyl methacrylate as one or more film forming agents; and (b) chlorhexidine or a salt thereof as a disinfectant; or (a) 2-ethoxyethyl methacrylate as one or more film forming agents; and (b) chlorhexidine digluconate as a disinfectant.

In an embodiment, the composition comprises:
(a) from 5 to 20% by weight in relation to the weight of the composition of one or more film formings;
(b) from 0.02 to 0.40% by weight in relation to the weight of the composition of chlorhexidine or a salt thereof as a disinfectant; and
(c) from 80 to 95% by weight of a solvent system comprising:
(c1) from 1 to 25% by weight in relation to the total weight of the solvent system of the water-immiscible solvents as defined above;
(c2) from 1 to 70% by weight in relation to the total weight of the solvent system of acetone;
(c3) from 5 to 70% by weight in relation to the total weight of the solvent system of $(C_2\text{-}C_3)$ alcohols as defined above;
(c4) from 0 to 20% by weight in relation to the total weight of the solvent system of one or more water-miscible solvent selected from water, glycol, and a mixture thereof;
being the sum of (c1), (c2), (c3) and (c4) up to 100% by weight in relation to the total weight of the solvent system; and
being the sum of (a), (b) and (c) up to 100% by weight in relation to the total weight of the composition; particularly,
(a) from 5 to 20% by weight in relation to the weight of the composition of 2-ethoxyethyl methacrylate as $(C_1\text{-}C_6)$alkoxy $(C_1\text{-}C_6)$ alkyl methacrylate film forming polymer; and
(b) from 0.02 to 0.40% by weight in relation to the weight of the composition of chlorhexidine or a salt thereof as a disinfectant; particularly chlorhexidine digluconate.
In an embodiment, the composition of the invention comprises:
(a) from 5 to 20% by weight in relation to the weight of the composition of one or more film formings;
(b) from 0.02 to 0.40% by weight in relation to the weight of the composition of chlorhexidine or a salt thereof as a disinfectant; and
(c) from 80 to 95% by weight of a solvent system comprising:
(c1) from 1 to 25% by weight in relation to the total weight of the solvent system of one or more water immiscible solvents (c1) selected from the group consisting of $(C_1\text{-}C_5)$alkyl-CO—O—$(C_1\text{-}C_6)$alkyl, $((C_1\text{-}C_6)$alkyl$)_3$Si—O—Si$((C_1\text{-}C_6)$alkyl$)_3$, and a mixture thereof:
(c2) from 1 to 70% by weight in relation to the total weight of the solvent system acetone;
(c3) from 5 to 70% by weight in relation to the total weight of the solvent system of one or more $(C_2\text{-}C_3)$ alcohols; particularly ethanol, isopropanol and a mixture thereof; and
(c4) from 0 to 20% by weight in relation to the total weight of the solvent system one or more water-miscible solvents selected from the group consisting of water, glycol, glycerine and a mixture thereof; being the sum of (c1), (c2), (c3) and (c4) up to 100% by weight in relation to the total weight of the solvent system; and
being the sum of (a), (b) and (c) up to 100% by weight in relation to the total weight of the composition; particularly, (a) from 5 to 20% by weight in relation to the weight of the composition of 2-ethoxyethyl methacrylate as $(C_1\text{-}C_6)$alkoxy $(C_1\text{-}C_6)$ alkyl methacrylate film forming polymer; and
(b) from 0.02 to 0.40% by weight in relation to the weight of the composition of chlorhexidine digluconate as a disinfectant.
In an embodiment, the composition of the invention comprises:
(a) from 5 to 20% by weight in relation to the weight of the composition of one or more film formings;
(b) from 0.02 to 0.40% by weight in relation to the weight of the composition of chlorhexidine or a salt thereof as a disinfectant; and
(c) from 80 to 95% by weight of a solvent system comprising:
(c1) from 1 to 25% by weight in relation to the total weight of the solvent system of one or more water immiscible solvents (c1) selected from the group consisting of $(C_1\text{-}C_5)$alkyl-CO—O—$(C_1\text{-}C_6)$alkyl, $((C_1\text{-}C_6)$alkyl$)_3$Si—O—Si$((C_1\text{-}C_6)$alkyl$)_3$, and a mixture thereof:
(c2) from 1 to 70% by weight in relation to the total weight of the solvent system of acetone;
(c3) from 5 to 70% by weight in relation to the total weight of the solvent system of one or more $(C_2\text{-}C_3)$ alcohols; particularly ethanol, isopropanol and a mixture thereof; and
(c4) from 0 to 20% by weight in relation to the total weight of the solvent system of a mixture of water and glycerine as water-miscible solvents;
being the sum of (c1), (c2), (c3) and (c4) up to 100% by weight in relation to the total weight of the solvent system; and
being the sum of (a), (b) and (c) up to 100% by weight in relation to the total weight of the composition; particularly,
(a) from 5 to 20% by weight in relation to the weight of the composition of 2-ethoxyethyl methacrylate as $(C_1\text{-}C_6)$alkoxy $(C_1\text{-}C_6)$ alkyl methacrylate film forming polymer; and
(b) from 0.02 to 0.40% by weight in relation to the weight of the composition of chlorhexidine digluconate as a disinfectant.
In an embodiment, the composition of the invention comprises:
(a) from 5 to 20% by weight in relation to the weight of the composition of one or more film formings;
(b) from 0.02 to 0.40% by weight in relation to the weight of the composition of chlorhexidine or a salt thereof as a disinfectant; and
(c) from 80 to 95% by weight of a solvent system comprising:
(c1) from 1 to 25% by weight in relation to the total weight of the solvent system of one or more of $(C_1\text{-}C_5)$alkyl-CO—O—$(C_1\text{-}C_6)$alkyl as water immiscible solvents;
(c2) from 1 to 70% by weight in relation to the total weight of the solvent system of acetone;
(c3) from 5 to 70% by weight in relation to the total weight of the solvent system of a mixture of ethanol and isopropanol as $(C_2\text{-}C_3)$ alcohols; and
(c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as $(C_1$-$C_6)$alkoxy $(C_1$-$C_6)$ alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of one or more of $(C_1$-$C_5)$alkyl-CO—O—$(C_1$-$C_6)$alkyl as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2$-$C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as $(C_1$-$C_6)$alkoxy $(C_1$-$C_6)$ alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of ethylacetate as $(C_1$-$C_5)$ alkyl-CO—O—$(C_1$-$C_6)$alkyl water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2$-$C_3)$ alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as $(C_1$-$C_6)$alkoxy $(C_1$-$C_6)$ alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of ethylacetate as $(C_1$-$C_5)$ alkyl-CO—O—$(C_1$-$C_6)$alkyl water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as $(C_2$-$C_3)$ alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as $(C_1$-$C_6)$alkoxy $(C_1$-$C_6)$ alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of a mixture of one or more of $(C_1$-$C_5)$alkyl-CO—O—$(C_1$-$C_6)$alkyl and $((C_1$-$C_6)$alkyl$)_3$Si—O—Si$((C_1$-$C_6)$alkyl$)_3$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as ($C_2$-$C_3$) alcohols; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as ($C_1$-$C_6$)alkoxy ($C_1$-$C_6$) alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of a mixture of one or more of ($C_1$-$C_5$)alkyl-CO—O—($C_1$-$C_6$)alkyl and (($C_1$-$C_6$)alkyl)$_3$Si—O—Si(($C_1$-$C_6$)alkyl)$_3$ as water immiscible solvents;

(c2) from 1 to 70% by weight in relation to the total weight of the solvent system of acetone;

(c3) from 5 to 70% by weight in relation to the total weight of the solvent system of a mixture of ethanol and isopropanol as ($C_2$-$C_3$) alcohols; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as ($C_1$-$C_6$)alkoxy ($C_1$-$C_6$) alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of a mixture of ethyl acetate and hexamethyldisiloxane as water immiscible solvents;

(c2) from 1 to 70% by weight in relation to the total weight of the solvent system of acetone;

(c3) from 5 to 70% by weight in relation to the total weight of the solvent system of one or more ($C_2$-$C_3$) alcohols; particularly ethanol, isopropanol and a mixture thereof; particularly isopropanol; and (c4) from 0 to 20% by weight in relation to the total weight of the solvent system of one or more water-miscible solvents selected from the group consisting of water, glycol, glycerine and a mixture thereof; being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as ($C_1$-$C_6$)alkoxy ($C_1$-$C_6$) alkyl methacrylate film forming polymer; and (b) from 0.02 to 0.40% by weight in relation to the weight of the composition of chlorhexidine digluconate as a disinfectant.

In an embodiment, the composition of the invention comprises:

(a) from 5 to 20% by weight in relation to the weight of the composition of one or more film formings;

(b) from 0.02 to 0.40% by weight in relation to the weight of the composition of chlorhexidine or a salt thereof as a disinfectant; and (c) from 80 to 95% by weight of a solvent system comprising:

(c1) from 1 to 25% by weight in relation to the total weight of the solvent system of a mixture of ethyl acetate and hexamethyldisiloxane as water immiscible solvents;

(c2) from 1 to 70% by weight in relation to the total weight of the solvent system of acetone;

(c3) from 5 to 70% by weight in relation to the total weight of the solvent system of one or more ($C_2$-$C_3$) alcohols; particularly ethanol, isopropanol and a mixture thereof; particularly isopropanol; and (c4) from 0 to 20% by weight in relation to the total weight of the solvent system of a mixture of water and glycerine as water-miscible solvents;

being the sum of (c1), (c2), (c3) and (c4) up to 100% by weight in relation to the total weight of the solvent system; and being the sum of (a), (b) and (c) up to 100% by weight in relation to the total weight of the composition; particularly, (a) from 5 to 20% by weight in relation to the weight of the composition of 2-ethoxyethyl methacrylate as ($C_1$-$C_6$)alkoxy ($C_1$-$C_6$) alkyl methacrylate film forming polymer; and (b) from 0.02 to 0.40% by weight in relation to the weight of the composition of chlorhexidine digluconate as a disinfectant.

As it is mentioned above, the composition of the invention comprises from 80 to 95% by weight of a solvent system; wherein (c3) is one or more ($C_2$-$C_3$) alcohols selected from the group consisting of ethanol, isopropanol and a mixture thereof. In an embodiment, the composition of the invention as defined above and below which comprises from 80 to 95% by weight of a solvent system; wherein (c3) is a mixture of ethanol and isopropanol and the amount of ethanol is from 1 to 99% by weight in relation to the total weight of (c3); and the amount of isopropanol is from 1 to 99% by weight in relation to the total weight of (c3).

As it is mentioned above, the composition of the invention comprises one or more (d) appropriate acceptable excipients or carriers. In an embodiment, the composition is a pharmaceutical composition comprising appropriate pharmaceutically acceptable excipients or carriers. In an embodiment, the composition is a cosmetic composition comprising appropriate cosmetic acceptable excipients or carriers. The term "pharmaceutically acceptable" refers to that excipients or carriers suitable for use in the pharmaceutical technology for preparing compositions with medical use. And the terms "cosmetically acceptable" or "dermatological acceptable" have the same meaning and which are herein used interchangeably. They refer to that excipients or carriers suitable for use in contact with human skin without undue toxicity, incompatibility, instability, allergic response, among others. The excipients or carriers used have affinity for the skin, are well tolerated, stable, and are used in an amount adequate to provide the desired consistency, and ease application. The appropriate excipients and/or carriers, and their amounts, can readily be determined by those skilled in the art according to the type of formulation being prepared to provide the desired consistency and ease application. Examples of appropriate excipients or carriers can include, but not limited to, propellant, pH adjusting agent, thickening agent, gelling agent, antioxidant, fragrance, colorant, opacifying agents, and mixture thereof.

The composition of the present invention can be in form of spray optionally comprising one or more propellants. In an embodiment, the topical composition of the present invention is in form of a spray, optionally comprising one or more propellants as defined below. The term "propellant" refers to one or more gases that are used to pressurize the composition to facilitate the pulverization of the composition from the container. Some propellants may be a mixture of gases (e.g., A-46 which is a mixture of isobutane, butane, and propane). A propellant may be in the form of a liquid (i.e., a liquefied gas) when under pressure within the reservoir of a spray device. In addition, a propellant may be in its gaseous state within the head space of the reservoir. A propellant may be present in both a liquefied form and its gaseous state within the reservoir. Unless specified otherwise (e.g., liquid propellant or gaseous propellant), the term propellant is intended to encompass the liquefied form and the gaseous state individually and collectively. Example of appropriate propellant include, but are not limited to, compressed air, nitrogen, inert gases, carbon dioxide, and mixtures thereof. Propellants may also include gaseous hydrocarbons like propane, n-butane, isobutane, isobutene, cyclopropane, and mixtures thereof. Halogenated hydrocarbons like 1,1-difluoroethane may also be used as propellants. Some non-limiting examples of propellants include 1,1,1,2, 2-pentafluoroethane, 1,1,1,2-tetrafluoroethane, 1,1,1,2,3,3, 3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17

(n-butane), A-108 (propane), AP70 (a mixture of propane, isobutane and n-butane), AP40 (a mixture of propane, isobutene and n-butane), AP30 (a mixture of propane, isobutane and n-butane), 152A (1,1 difluoroethane), and PROPEL-45 (a mixture of isobutane, propane and butane). If present, the amount of the propellant is from 25 to 75% by weight. In an embodiment, the topical composition of the present invention is in form of a spray, and the composition further comprises one or more propellants as defined above, particularly a propellant other than chlorofluorocarbons containing compounds, such as dimethyl ether or propane.

The terms "pH adjusting agent", "pH adjuster" and "pH regulating agent" and "buffer" and "buffering agent" have the same meaning and are used interchangeable. They refer to a substance that actively adjust and regulates the pH value of a solution to which they have been added. The commonly used pH regulating agents can include, but are not limited to, strong acids (i.e., acids that are completely dissociated in aqueous solution) and strong bases (i.e., bases that are completely dissociated in aqueous solution), acidic buffering agents and alkaline buffering agents, and nicotine. Examples of pH adjuster includes, but not limited to, sodium citrate, citric acid, dehydroacetic acid or a salt thereof, lactic acid, sodium hydroxide, triethanolamine and mixture thereof. If present, the amount of pH regulating agent is up to 0.5% by weight.

The term "thickening agent" or "thickener" or "viscosity agent" or "viscosity controlling" which is herein used interchangeably refers to a material that increases its viscosity without substantially modifying its other properties. Appropriate thickener includes, but are not limited to, natural and synthetic or semi-synthetic thickeners which derive from various sources and consist of very different molecular structures including polysaccharides, proteins, and alcohols. Examples of appropriate thickener include cetyl alcohol, stearyl alcohol, stearic acid, cellulose derivatives such as hydroxyethylcellulose, guar gum, locust bean gum, xanthan gum, gelatine, and polymeric compounds such as acrylic-based polymer (carbomer). If present, the amount of the viscosity agent up to 2% by weight.

The term "gelling agent" refers to any substance which, when combined with the other components of the composition, increases the gelatinous quality or viscosity of the composition. Examples of gelling agents can include, but are not limited to, alginates, gelatines, pectines and a mixture thereof. If present, the amount of gelling agent is up to 2% by weight.

The term "antioxidant" refers to any substance that delays or prevents the oxidation of any oxidizable component of the composition, such as for example fatty or oil components. Examples of antioxidants can include, but are not limited to, vitamin C, vitamin E such as tocopheryl acetate, vitamin A, niacinamide, butylated hydroxy-toluene (BHT), butylated hydroxyanisol (BHA), hydroxyacetophenone and mixture thereof. If present, the amount of antioxidants is up to 1%% by weight.

The term "opacifying agent" refers to any substance that becomes a composition or a product opaque or that enhances the opacity of said composition or product. Examples of opacifying agent suitable for the present invention, but are not limited to, titanium dioxide, ozokerite, cetearyl alcohol, mica, tin oxide, cera microcristallina, ceresin, silica, cetyl alcohol, talc, styrene/acrylates copolymer, stearyl alcohol, hydrated silica, glycol distearate, myristyl myristate, nylon-12, glycol stearate, boron nitride, kaolin, magnesium aluminum silicate, alumina, propylene glycol stearate SE, methyl methacrylate, and mixture thereof. If present, the amount of opacifying agent is up to 2% by weight.

In an embodiment, composition of the present invention is a topical composition comprising one or more appropriate topical pharmaceutically or cosmetically acceptable excipients or carriers. In an embodiment, the composition of the present invention is a topical pharmaceutical or cosmetic composition comprising one or more appropriate topical pharmaceutically or cosmetically acceptable excipients or carriers. The topical compositions of the invention can be formulated in several forms that include, but are not limited to, creams, stick, roll-on, spray, soft solids, gels, mousses, ointments, and pastes. Typically these topical compositions can be applicable by means of a spray, roll-on, drop tip, brush or spatula.

As it is mentioned above, the composition of the present invention can be a drug delivery system, then the composition of the present invention can further comprise one or more additional active ingredients; particularly, one or more pharmaceutically or cosmetically active ingredients. The presence of additional active ingredients and its amount can readily be determined by those skilled in the art according to the type of formulation being prepared to provide the appropriate pharmaceutically or cosmetically effect. Examples of appropriate additional active ingredients can include, but are not limited to, anti-inflammatory agents, anticoagulant agents, antibiotic, fungicide, viricide, sunscreen, biocide, anesthetic, analgesic, healing agents and a mixture thereof. If present, the amount of additional pharmaceutically or cosmetically active ingredients is up to 2.0% by weight. It seems that due to the bioadhesion and the physico-chemical environment properties of the film formed onto the target skin/hair/nail surface, the additional active ingredients can diffuse from the film and penetrates the skin/hair/nail.

As it is mentioned above, the composition of the invention is capable of creating an in-situ film upon contact with a surface having appropriate physical and mechanical properties as well as suitable desinfectant activity using only gentle components that comply with the requirements of health authorities without the need of phthalate containing compounds.

In an embodiment, the composition of the present invention is "substantially free" of phthalate containing compounds; latex containing compounds; or phthalate containing compounds and latex containing compounds. In an embodiment, the composition of the present invention is "free" of phthalate containing compounds, latex containing compounds, or phthalate containing compounds and latex containing compounds. In an embodiment, the composition of the present invention is "substantially free" of "phthalates". For the purpose of the invention, the terms "phthalates", "phthalate components" and "phthalate containing compounds" have the same meaning and are used interchangeable. They encompass the phthalic free acid and any mono- or di-$(C_1-C_{20})$alkyl or aryl ester thereof. For the purpose of the invention, the term "phthalate" encompasses dimethyl phthalate, diethyl phthalate, dicyclohexyl phthalate, diisodecyl phthalate, dibutyl phthalate and dibenzyl phthalate. In an embodiment, the composition of the present invention is "substantially free" of "latex". For the purpose of the invention, the terms "latex" and "latex containing compounds" have the same meaning and are used interchangeable. They refer to a colloidal aqueous suspension composed of some fats, waxes and various gummy resins obtained from the cytoplasm of laticiferous cells present in some angiosperm plants and fungi. Latex is frequently white, although it can also present orange, reddish or yellowish depending on the species, and milky in appearance. For the purpose of the invention, the term "latex" encompasses natural latex, semisynthetic latex, and synthetic latex. In an embodiment, the composition of the present invention is "substantially free" of "phthalates" and "latex" as defined above. For the purpose of the invention, the term "substantially free" refers to a composition comprises less than 0,003% by weight of phthalates, latex, or the sum of the amounts of phthalates and latex. In an embodiment, the composition of the invention is "free" of phthalates, latex, or both. The term "free of" refers to a composition whose content of phthalates, or latex or both is not detectable by any of the commonly used techniques defined in the state of the art. For the purpose of the invention, the method for determining the content of phthalates can be by high performance liquid chromatography (HPLC) after dilution and filtration of the sample containing it.

It is also an aspect of the invention, a process for the preparation of the composition of the first aspect of the invention. The appropriate process can readily be determined by those skilled in the art from those disclosed in the state of the art according to the type of formulation being prepared. Typically, the process for the preparation of solutions comprises mixing all the ingredients until the completely dissolution of the ingredients. By way of illustration, the composition of the invention can be prepared following the general process as defined herein below:

(i) preparation of mixture 1: mixing the disinfectant with the $(C_2-C_3)$ alcohol; preferably iso-propanol, ethanol, or a mixture thereof, and optionally one or more water-miscible solvents; particularly water, glycerine, or a mixture thereof;

(ii) preparation of mixture 2: mixing the film-forming, the acetone, the water-immiscible solvents, and the alcohols; preferably ethanol, (iii) mixture 2 was added to mixture 1 and the resulting mixture was maintained under agitation to obtain the composition of the first aspect of the invention.

In an embodiment, when the composition further comprises additional excipients of carriers, they can be added to the resulting mixture of step (i), or alternatively to the resulting mixture of step (ii) or alternatively to the resulting mixture of step (iii). In fact, the process for the incorporation of the additional excipients or carriers can readily be determined by those skilled in the art, according to the type of excipient or carrier and the type of formulation being prepared.

In an embodiment step (i) of the process for the preparation of the composition of the invention is performed at room temperature. In an embodiment step (i) of the process for the preparation of the composition of the invention is agitated for the appropriate time until having a clear solution; particularly from 5 to 30 min. In an embodiment step (ii) of the process for the preparation of the composition of the invention is performed at room temperature. In an embodiment step (ii) of the process for the preparation of the composition of the invention is perfumed by mixing solution (i) and (ii) and stirring the mixture thus obtained for at least 10 min. The term "room temperature" refers to a temperature of the environment, without heating or cooling, and is generally comprised from 20° C. to 25° C.

Further, when the composition of the invention is in form of spray, the process further comprises an additional step (iv) comprising mixing the composition obtained in step (iii) with the one or more propellants into an appropriate container.

The composition of the present invention can be defined by its preparation process. Thus, a composition of the first aspect of the invention obtainable by the process as defined above is also part of the invention. For the purposes of the invention the expressions "obtainable", "obtained" and equivalent expressions are used interchangeably, and in any case, the expression "obtainable" encompasses the expression "obtained". All the embodiments disclosed above for the process of the invention applies also for the composition obtainable by this process.

The second aspect of the invention relates to the use of the composition of the present invention as film-forming agent, particularly by depositing the composition on a surface to be filmed. In particular, the composition of the invention is suitable for forming an in-situ adherent film. In an embodiment, the composition of the invention is suitable for forming an in-situ adherent film selected from the group consisting of in-situ film dressing and an in-situ fixation film.

Thus, the third aspect of the invention is an adherent film comprising: (a) the one or more film forming agents and (b) the one or more disinfectants as defined in the present application of the composition of the first aspect of the invention which is obtainable in-situ by applying the composition as defined in the first aspect of the invention over the surface to be filmed under such conditions that allows obtaining the film.

In an embodiment, the adherent film comprises:
(a) one or more film forming polymers selected from the group consisting of (C$_1$-C$_6$)alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$)alkyl methacrylate; copolymers thereof; copolymers of one of (C$_1$-C$_6$)alkyl acrylate based polymers; (C$_1$-C$_6$)alkyl methacrylate based polymers; (C$_1$-C$_6$)alkoxy (C$_1$-C$_6$) alkyl acrylate based polymers; (C$_1$-C$_6$)alkoxy (C$_1$-C$_6$) alkyl methacrylate based polymers, hydroxy(C$_1$-C$_6$) alkyl acrylate, hydroxy(C$_1$-C$_6$)alkyl methacrylate with methacrylic acid; copolymers of one of (C$_1$-C$_6$)alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$)alkyl methacrylate with acrylic acid; copolymers of one of (C$_1$-C$_6$)alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$) alkyl methacrylate with acrylamide; mono-acrylates of glycols and poly glycols; mono-methacrylates of glycols and polyglycols; glycidyl acrylate based polymers; and glycidyl methacrylate based polymers with acrylamide; and
(b) one or more (C$_1$-C$_6$)alkyl N(alpha)-(C$_{10}$-C$_{25}$)alkanoyl-L-arginate disinfectant or a salt thereof; particularly (C$_1$-C$_6$)alkyl lauroyl arginate or a salt thereof; particularly hydrochloride salt.
In an embodiment, the adherent film comprises:
(a) one or more (C$_1$-C$_6$)alkoxy (C$_1$-C$_6$) alkyl methacrylate as film forming polymers; and
(b) one or more (C$_1$-C$_6$)alkyl N(alpha)-(C$_{10}$-C$_{25}$)alkanoyl-L-arginate disinfectant or a salt thereof; particularly (C$_1$-C$_6$)alkyl lauroyl arginate or a salt thereof; particularly hydrochloride salt.

In an embodiment, the adherent film comprises:
(a) 2-ethoxyethyl methacrylate as (C$_1$-C$_6$)alkoxy (C$_1$-C$_6$) alkyl methacrylate film forming polymer; and
(b) ethyl lauroyl arginate or a salt thereof; particularly hydrochloride salt, as disinfectant.
In an embodiment, the adherent film comprises:
(a) one or more (C$_1$-C$_6$)alkoxy (C$_1$-C$_6$) alkyl methacrylate as film forming polymers; and
(b) chlorhexidine or a salt thereof as a disinfectant; particularly chlorhexidine digluconate.
In an embodiment, the adherent film comprises:
(a) 2-ethoxyethyl methacrylate as (C$_1$-C$_6$)alkoxy (C$_1$-C$_6$) alkyl methacrylate film forming polymer; and
(b) chlorhexidine or a salt thereof as a disinfectant; particularly chlorhexidine digluconate.
In an embodiment, the adherent film comprises:
(a) from 92% to 99.95% by weight in relation to the weight of the film of one or more film forming agents as defined above and below; and
(b) from 0.05 to 4% by weight in relation to the weight of the film of one or more disinfectants as defined above and below;
being the sum of the all ingredients of the film up to 100% by weight in relation to the weight of the film.
In an embodiment, the adherent film comprises:
(a) from 92% to 99.95% by weight in relation to the weight of (C$_1$-C$_6$)alkoxy (C$_1$-C$_6$) alkyl methacrylate polymers as the one or more film forming agents; and
(b) from 0.05% to 4% by weight in relation to the weight of the film of (C$_1$-C$_6$)alkyl N(alpha)-(C$_{10}$-C$_{25}$)alkanoyl-L-arginate as the one or more disinfectants;
being the sum of the all ingredients of the film up to 100% by weight of the weight of the film.
In an embodiment, the adherent film comprises:
(a) from 92% to 99.95% by weight in relation to the weight of 2-ethoxyethyl methacrylate as (C$_1$-C$_6$)alkoxy (C$_1$-C$_6$) alkyl methacrylate film forming polymer; and
(b) from 0.05% to 4% by weight in relation to the weight of the film of ethyl lauroyl arginate or a salt thereof; particularly hydrochloride salt, as disinfectant;
being the sum of the all ingredients of the film up to 100% by weight of the weight of the film.
In an embodiment, the adherent film comprises:
(a) from 92% to 99.95% by weight in relation to the weight of (C$_1$-C$_6$)alkoxy (C$_1$-C$_6$) alkyl methacrylate polymers as the one or more film forming agents; and
(b) from 0.05% to 4% by weight in relation to the weight of the film of chlorhexidine or a salt thereof as a disinfectant; particularly chlorhexidine digluconate;
being the sum of the all ingredients of the film up to 100% by weight of the weight of the film.
In an embodiment, the adherent film comprises:
(a) from 92% to 99.95% by weight in relation to the weight of 2-ethoxyethyl methacrylate as (C$_1$-C$_6$)alkoxy (C$_1$-C$_6$) alkyl methacrylate film forming polymer; and
(b) from 0.05% to 4% by weight in relation to the weight of the film of chlorhexidine or a salt thereof as a disinfectant; particularly chlorhexidine digluconate;
being the sum of the all ingredients of the film up to 100% by weight of the weight of the film.
All the embodiments disclosed above for the composition of the first aspect of the invention, particularly to the film-forming agents (a) and the disinfectants (b) apply also for adherent film of the third aspect of the invention.

In an embodiment, the adherent film of the present invention is one wherein the surface to be filmed is selected from a living surface or a non-living surface. The terms "non-living surface" and "abiotic surface" have the same meaning and they are used interchangeable, They refers to any surface which is different from a surface of a human or animal living body (i.e, skin, tissue, mucosa). Examples of non-living surface include, but without limitation, tracks, catheter tracts, bandages and sticks. The term non-living surface" also encompasses dead human or animal body.

In an embodiment, the adherent film of the present invention is an in-situ adherent film selected from the group consisting of in-situ film dressing and an in-situ fixation film.

As it is mentioned above, the composition of the invention is suitable for forming an in-situ film dressing. The term "film dressing" refers to a film applied to a tissue (particularly the skin) to protect and/or promote their healing. The dressing is designed to be in direct contact with the skin, particularly directly in contact with the wound or burned area, as distinguished from a bandage, which is most often used to hold a dressing in place. It is also part of the invention, the composition capable of forming the in-situ film dressing or alternatively the in-situ film dressing thus obtainable for use in therapy. In an embodiment, the composition capable of forming the in-situ film dressing or alternatively the in-situ film dressing thus obtainable for use in the treatment or prevention of tissue and organs injuries. In an embodiment, the composition capable of forming the in-situ film dressing or alternatively the in-situ film dressing thus obtainable for use in the treatment or prevention of tissue and organs injuries selected from the group consisting of wound healing, burn healing, skin blisters, chafing, sunlight damage, insect bites, punctures and vaccinations.

It is also part of the invention, the use of the composition capable of forming the in-situ film dressing or alternatively the in-situ film dressing thus obtainable in cosmetics.

In an embodiment, the composition of the invention capable of forming the in-situ film dressing or alternatively the in-situ film dressing thus obtainable is suitable for forming an in-situ fixation film. The term "fixation film" refers to a film capable of fixing or gluing one surface to another in order to reduce, minimize or avoid the movement between them. The fixation is performed in-situ after the application of the composition of the invention either between tissues or between different parts of a unique tissue; or alternatively between one or more tissues and medical/surgical material such as fixation of drain tracks, catheter tracts, bandages and sticks; and for ostomy material fixation. The in-situ film of the present invention has the advantage of being biocompatible, non-irritant, and having the appropriate adhesion properties for being used as fixing agent.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. Compositions of the Invention

1.1. Compositions in Form of Spray

1.1.1. Compositions of the Present Invention (Examples 1-5 and Examples 1'-5')

These examples illustrate compositions in form of spray in accordance with the present invention. The compositions of the present invention can be in form of pressurized sprays 1-5 which comprises one or more propellant gasses; or in form non-pressurized sprays 1'-5' which do not comprise propellant gasses. Table 1 shows the qualitive and quantitative composition of Examples 1-5 forming part of the sprays of the present invention. In particular, the amount of each ingredient expressed in percentage (%) by weight in relation to the total weight of the composition is detailed in Table 1.

TABLE 1

| Function | Ingredient | Comp. 1 | Comp. 2 | Comp. 3 | Comp. 4 | Comp. 5 |
|---|---|---|---|---|---|---|
| Film forming agent (a) | Polyethoxy-ethyl methacrylate (PEEMA) | 8.8% | 8.8% | 8.8% | 8.8% | 8.8% |
| Disinfectant (b) | Ethyl lauroyl arginate hydrochloride salt | 0.1%[a] | 0.1%[b] | 0.045%[c] | — | — |
| | Chlorhexidine base | — | — | — | 0.056%[d] | — |
| | Chlorhexidine digluconate | — | — | — | — | 0.1%[e] |
| Solvent system (c) | Ethyl acetate (c1) | 14.3% | 14.3% | 14.2% | 14.3% | 14.3% |
| | Hexamethyldisiloxane (c1) | — | — | 41% | — | — |
| | Acetone (c2) | 35% | 26% | 20% | 26% | 26% |
| | 2-propanol (c3) | 5% | 13.2% | 15.55% | 13.2% | 13.2% |
| | Etanol (c3) | 34% | 19.7% | — | 19.7% | 19.7% |
| | Purified water (c4) | 2.8% | 17.5% | 0.225% | 17.944 | 17.9%[e] |
| | Glicerine (c4) | — | 0.4%[b] | 0.18%[c] | — | — |
| | Total amount (%) by weight | 100% | 100% | 100% | 100% | 100% |

[a]Provided as pure solid form

[b]Provided from a 0.5% of a solution of LAE 20% w/w in glycerine (AMINAT-G ®). It is equivalent to a 0.1% of LAE and 0.4% of Glycerine.

[c]Provided from a 0.225% of a solution of LAE 20% w/w in glycerine (AMINAT-G ®). It is equivalent to a 0.045% of LAE and 0.18% of Glycerine.

[d]This amount of chlorhexidine base is equivalent to a 0.1% of chlorexidine digluconate salt (CHG).

[e]Provided from a 0.5% of a 20% aqueous solution of chlorhexidine digluconate (CHG). It is equivalent to a 0.1% of CHG and an extra 0.4% of water (17.5% + 0.4% = 17.9%).

To sum up, pressurized sprays 1-5 comprises compositions 1-5 disclosed in Table 1 respectively and one or more propellant gasses; and non-pressurized sprays 1'-5' only contains compositions 1-5 disclosed in Table 1 respectively without propellant gasses.

Table 2 shows the qualitive and quantitative composition of pressurized Sprays 1-5 of the present invention containing the film-forming composition (examples 1-5) of the present invention respectively disclosed in Table 1.

TABLE 2

| INGREDIENTS | FUNCTION | % BY WEIGHT |
|---|---|---|
| Composition of the present invention (Examples 1-5) | Film-forming composition | 47% |
| Dimethylether (DME) | Propellant | 53% |

1.1.2. Preparation Process

Compositions of Example 1-5

Example 1

(i) The disinfectant in solid form was mixed under agitation with water and 2-propanol to obtain a mixture 1.

(ii) A solution of the film-forming agent was prepared under agitation in the corresponding amount of ethyl acetate, acetone and ethanol to obtain a mixture 2.

(iii) Mixture 1 was added to mixture 2 and maintained under agitation until obtaining composition 1 of Table 1 of the present invention.

Examples 2-5

The compositions of Examples 2-5 were prepared following the process as defined above for composition 1, but in step (i) the disinfectant was in solution form instead of in solid form and it was mixed with water, 2-propanol and optionally glicerine to obtain mixture 1. And, in step (ii) the solution of film-forming agent was prepared by mixing ethyl acetate, acetone, and optionally ethanol and/or hexamethyldisiloxane.

Sprays

Pressurized Sprays 1-5

The pressurized spray composition 1-5 of the present invention disclosed in Table 2 was prepared following the process disclosed herein below.

The composition 1-5 was loaded into a container and charged with the percentage by weight of propellant mixture disclosed in Table 2. The loaded containers were sealed with a valve which is provided with a cannula and a spray nozzle.

Non-Pressurized Sprays 1'-5'

The non-pressurized sprays 1'-5' of the present invention comprising only the compositions 1-5 of the present invention respectively, were prepared as defined above with the pressurized sprays but without adding propellant gas. Therefore, the process comprises loading the container with the composition of the invention and sealing the container with a spray nozzle with a cannula.

1.2.1. Comparative Composition Falling Outside the Scope of the Present Invention (Comparative Example 1)

This comparative example illustrates the comparative composition in form of spray falling outside the scope of the present invention commercially available in 2020 with the marketed name Nobecutan®. In particular, the amount of each ingredient expressed in percentage (%) by weight in relation to the total weight of the composition is detailed in Table 3.

TABLE 3

| function | Ingredient | Comp. Composition 1NOBECUTAN ® (marketed in 2020) |
|---|---|---|
| Film forming agent (a) | Polyethoxy-ethyl methacrylate (PEEMA) | 8.8% |
| Disinfectant (b) | Tetramethylthiuram disulfide (TMTD) | 0.05% |
| Solvent system (c) | Ethylacetate (c1) | 91.15% |
| | Acetone (c2) | — |
| | 2-propanol (c3) | — |
| | Etanol (c3) | — |
| | Purified water (c4) | — |
| | Total amount (%) by weight | 100% |

The comparative composition Example 1 can be forming part of a pressurized spray (comparative pressurized spray 1) or forming part of a non-pressurized spray (comparative non-pressurized spray 1'). Analogously as above, the comparative pressurized spray 1 further comprises a propellant gas. Table 4 shows the qualitive and quantitative composition of comparative spray 1 falling outside of the scope of the present invention containing the comparative film-forming composition (comparative example 1) disclosed in Table 3 and the propellant gas.

TABLE 4

| INGREDIENTS | FUNCTION | % BY WEIGHT |
|---|---|---|
| Comparative composition 1 (NOBECUTAN) | Film-forming composition | 47% |
| Dimethylether (DME) | Propellant | 53% |

1.1.2. Preparation Process

Comparative Composition 1

(i) The disinfectant in solid form was mixed under agitation with the sufficient amount of ethyl acetate for the dissolution of the disinfectant to obtain a mixture 1.

(ii) The film-forming agent is mixed under agitation with the remaining amount of ethyl acetate disclosed above to obtain mixture 2; and (iii) Mixture 2 was added to mixture 1 and maintained under agitation until obtaining the comparative composition 1.

Comparative Spray

Comparative Pressurized Spray 1

The pressurized comparative spray 1 disclosed in Table 4 was prepared following the process disclosed herein below. The comparative composition 1 was loaded into a container and charged with the percentage by weight of propellant mixture disclosed in Table 4. The loaded containers were sealed with a valve which is provided with a cannula and a spray nozzle.

Comparative Non-Pressurized Spray 1'

The comparative non-pressurized spray 1' only comprising the comparative composition 1, was prepared as defined above for the comparative pressurized spray 1 but without adding propellant gas. Therefore, the process comprises loading the container with the comparative composition 1 and sealing the container with a spray nozzle with a cannula.

2. Stability Test

The aim of this test is the assessment of the stability of the compositions of the invention. Therefore, the composition 1 of the present invention was loaded in a transparent container and also in metallic containers coated internally with different coatings.

2.1. Transparent Glass Container Test

Pressurized Spray 1 was loaded in transparent glass containers. Some of these containers with the pressurized Spray 1 were maintained in the container for 24 hours at room temperature. After that time, the effect of the propellent gas over the solubility of the components was analysed.

In fact, after performing this test, it was observed that the amount of the propellant gas DME (53% by weight) was perfectly admitted in the composition without causing precipitation or generation of new phases or dissolution cuts.

Other containers with the pressurized Spray 1 were maintained at 50° C. in an oven for 3 months. The appearances of the mixture content and the total weight of each container were periodically controlled without observing any separation or precipitation of phases, the mixture was always stable, no colour was developed and non-degradation was observed, indicating full compatibility with the propellant gas.

2.2. Metallic Coated Container

This test allows analysing the compatibility of the compositions of the invention with a container internally coated with polyamide (one of the most commonly used coatings for spray containers). In particular, the containers were formed by the valve, the pulverizer container and the cup being the container internally coated with polyamide.

A. Compatibility Tests Between the Film-Forming Composition 1 of the Present Invention and the Polyamide Lacquer, Stability of the Lacquer, Expansion Test of the Valve Seal and Behavior of the Spraying System Full containers loaded with Spray 1 of the present invention were tested. Haft of them were controlled for 3 months at room temperature and the other half, in parallel, were simultaneously introduced in an oven at 50° C. also during 3 months to evaluate accelerated stability; each month, one of the containers at room temperature and also one of the containers at 50° C. were removed and then, its accelerated stability was analysed until the third month, at which time this accelerated study was concluded.

Results: Polyamide-coated containers loaded with the composition of the invention successfully withstood all compatibility tests. Thus, no aerosol leaks and no corrosion were detected on the valve dome or the polyamide coating; even after 3 months at 50° C. Furthermore, the stability test mentioned above was also performed at 40° C., obtaining satisfactory results even after 6 months. Therefore, all these results allows fixing as expiration date the maximum time period allowed by the health authorities that is 5 years at conservation conditions of between 5° C. and 30° C. preferably, but being also able to choose between 5° C. and 40° C. in climatic zone Ill or IV; without alteration of either the composition and the container.

Besides, the stability of the disinfectant (LAE) present in the composition of Example 1 of the present invention in contact with the polyamide lacquer of the container was measured. Full containers loaded with Spray 1 of the present invention were controlled at 50° C. for 3 months, at 40° C. form 4 to 9 months, and at 30° C. from 6 to 18 months. After that time, the composition was applied to a surface to form the adherent film, in which the amount of LAE was calculated (mg of LAE/g of film).

The method for calculating the amount of LAE consists of a liquid chromatography-mass spectrometry (LC-MS) analysis of the tested sample previously sprayed into a container (glass flask) and dried into a rotary evaporator. The exact and constant weight of the residue is determined. This residue is dissolved in Acetonitrile and doped with a known volume solution of a solution f the internal pattern (Dodine, commercially available) in a known concentration. Then it is stirred and then, pure water at pH 3-4 (acidified with HCl) is added still flushing, this allows precipitating the polymer. The supernatant is filtered and punctured by LC-MS.

Equipment LC-MC

Detector: ACQ-QDa mass Detector
Column: Kromasil 100-5-C18 150×4.0 mm. (5 μm, 100 Å)
System design: Mobil phase entrance-Column-PDA entrance-QDa entrance-Waste Exit

LC-MC Conditions

Fluxe: 1.00 mL/min. (Path 2)
Injection volume: 8.0 μl
Column temperature: 30° C.±5° C.
Chromatogram duration: 15 minutes

47

Mobil phase: isocratic (acetonitrile LC-MS quality:water MilliQ+0.15% trifluoroacetic acid HPLC quality, 50:50)

Probe temperature: 600° C.

Gain: 1

Sampling rate: 1 (points/s)

Positive capillary voltage: 0.8 Kv

Cone voltage: 15 V

Function 1: SIR (Selected Ion Recording) m/z value.

Name m/z

LAE 385.30

Dodine 228.30

The obtained results demonstrated that the concentration of the disinfectant (LAE) was measured showing that only a reduction of about 11% of the amount of disinfectant after 3 months at 50° C. was detected.

3. Biocide Test

3.1. Microbiology Test

3.1.1. Microbiological Challenge Testing

Samples: This study was performed with the compositions of the present invention (Examples 1, 2, 4 and 5) and the comparative Example 1 (nobecutan)

Method: Microbiological Challenge Test is an Antimicrobial effectiveness test for topically used products and non-sterile nasal products following the Method USP <51> Preservative Challenge Test of May 1, 2018 included in the 2021 edition. Each composition was inoculated with the following strains of bacteria and fungi and monitored at 14 and 28 day:

*Pseudomonas aeruginosa* ATCC 9027

*Staphylococcus aureus* ATCC 6538

*Escherichia coli* ATCC 8739

*Candida albicans* ATCC 10231

*Aspergillus brasiliensis* ATCC 16404

The inoculated composition was maintained at a temperature between 20-25° C., protected from light during the test period.

Results: The results observed for all tested compositions were satisfactory and all met the acceptance criteria, reducing the population almost entirely

48

3.1.2. Microbiological Halos of Inhibition Testing

Samples: This study was performed with the compositions of the present invention (Examples 1, 2, 4 and 5) and the comparative Example 1 (nobecutan)

Method: The method used was based on the method from Ph. Eur. (10.4) 2.7.2 Microbiological Assay of Antibiotics wherein the test sample (200 ml) was introduced in a well within a seed layer with 10 cfu/ml of test.

The incubation conditions are detailed herein below. The bacterial strains were incubated 24 h at 37±1° C. in Tryptone Soya Agar; the yeast strains were incubated 24 h at 30±1° C. in Sabouraud Dextrose Agar; and the Mold strains were incubated 72 h at 30±1° C. in Sabouraud Dextrose Agar.

The strains used in the present test are listed herein below:

*Pseudomonas aeruginosa* ATCC 9027

*Staphylococcus aureus* ATCC 6538

*Escherichia coli* ATCC 8739

*Candida albicans* ATCC 10231

*Aspergillus brasiliensis* ATCC 16404

Results: the Halos of Inhibition of each composition is expressed in mm in the following Table:

| | Composition | | | | |
| Strains | Comparative Example 1 | Composition 1 | Composition 2 | Composition 4 | Composition 5 |
| --- | --- | --- | --- | --- | --- |
| Pseudomonas aeruginosa ATCC 9027 | 11 | 23 | 20 | 23 | 23 |
| *Staphylococcus aureus* ATCC 6538 | 9 | 15 | 14 | 19 | 21 |
| *Escherichia coli* ATCC 8739 | 11 | 14 | 14 | 20 | 20 |
| Candida albicans ATCC 10231 | 13 | 22 | 14 | 16 | 17 |
| Aspergillus brasiliensis ATCC 16404 | 0 | 15 | 10 | 11 | 12 |

As it is show in the Table Above, the compositions of the invention has a higher desinfectant (biocide) activity than the comparative composition. In fact, it is observed a higher biocide effect in all the tested strains even with *Aspergillus brasiliensis.*

4. Drying Speed Test

Sample: This study was performed with the compositions of Examples 1-5 of the present invention and the comparative Example 1 (Nobecutan).

Method: The method involved the application of the tested compositions onto skin of volunteers by the application of the non-pressurized sprays 1'-5' comprising the compositions of Examples 1-5 respectively, the pressurized spray composition 1 of the present invention comprising the composition of Example 1 or the comparative pressurized spray 1 comprising comparative composition 1 and propellant mixture and non-pressurized spray 1' comprising comparative composition 1 without propellant mixture.

Results: the drying speed of the tested compositions is summarized herein below:

| | Composition | Drying speed (t) |
|---|---|---|
| Non-pressurized spray | Comparative Spray 1' Comparative composition Example 1 | 2 min |
| | Spray 1' Composition 1 | 2 min 30 s |
| | Spray 2' Composition 2 | 3 min |
| | Spray 3' Composition 3 | 3 min |
| | Spray 4' Composition 4 | 3 min |
| | Spray 5' Composition 5 | 3 min |
| Pressurized spray | Comparative Spray 1 Comparative composition Example 1 | 1 min 15 s |
| | Spray 1 Composition 1 | 1 min 30 s |

As it is shown in Table below, the composition of the present invention has a comparable drying speed as the commercial comparative composition (Nobecutan).

5. Cutaneous Permeability Test

The pressurized spray 1 comprising the composition 1 of the present invention was pulverized onto a surface until having a film of 0.1 mm of thickness. The film thus obtained was then applied to a Payne cup containing distilled water. The cup containing the distilled water was then carefully weighed twice a day during a period of 24 hours. After approximately 24 hours, the evaporation of water per diem was constant and the diffusion through the film in mg/cm$^2$ during 24 h was calculated.

In particular, the adherent film of 0.1 mm of thickness obtained after application of the composition of Example 1 of the present invention allows for the diffusion of 65 mg of vapor per square centimeter through the film during a period of 24 hours.

Therefore, it is demonstrated that the in-situ adherent film of the present invention allows perspiration of the skin without compromising the impermeability of the film to water. In fact, the adherent film of the invention is permeable to steam and humidity but impermeable to water, thus preventing maceration of the treated area allowing at the same time bathing and personal hygiene.

6. Fracture Resistance Test

Spraying a previously tared aluminum plate (P1) with a sufficient amount of the composition of Example 1 of the present invention until obtained the adherent film of the invention and dry (by evaporation of the solvents) until constant weight in a vacuum oven at 40° C. for 20 min. Then, left temper and weigh the aluminum plate with the film (P2).

Repeat the evaporation operation for another 20 minutes and once tempered, weigh again the aluminium plate with the film (P3). The difference in recorded residue weights between the beginning and the end of the last evaporation/tempering cycle (PR1 and PR2) must be less than 0.5% of the lowest recorded weight, otherwise another evaporation/tempering cycle must be carried outed until meeting the above-mentioned requirement. The difference is calculated using the following formula:

$$\% \Delta P = \frac{|P_{R2} - P_{R1}|}{P_{R2}} \times 100$$

wherein:

$P_1$ (g): Aluminum plate weight.

$P_2$ (g): Aluminum plate weight+weight of the film previous the last evaporation/tempering cycle $P_3$ (g): Aluminum plate weight+weight of the film after the last evaporation/tempering cycle $P_{R1}$ (g)=$P_2$−$P_1$: weight of the film previous the last evaporation/tempering cycle $P_{R2}$ (g)=$P_3$−$P_1$: weight of the film after the last evaporation/tempering cycle % ΔP=weight lost percentage of the film between $P_{R2}$ and $P_{R1}$ Then, the elasticity and malleability of the last dried film obtained in previous test was measured. In fact, the dried film was taken between two tweezers and it was stretched from both tweezers with opposite forces outwards to cause the deformation of the film. This test demonstrated that the adherent film of the present invention is solid (it stretches but without brittle), elastic, deformable and capable of adapting the shape without being rigid,

CITATION LIST

Ph. Eur. (10.4) 2.7.2 Microbiological Assay of Antibiotics

For reasons of completeness, various aspects of the invention are set out in the following numbered clauses:

Clause 1. A composition comprising:

(a) one or more film forming agents;

(b) one or more disinfectant;

(c) a solvent system comprising:

(c1) one or more water immiscible solvents selected from the group consisting of (C$_1$-C$_5$)alkyl-CO—O—(C$_1$-C$_6$)alkyl, ((C$_1$-C$_6$)alkyl)$_3$Si—O—Si((C$_1$-C$_6$)alkyl)$_3$, (C$_1$-C$_5$)alkyl-O—(C$_2$-C$_5$)alkyl and a mixture thereof;

(c2) acetone; and (c3) one or more (C$_2$-C$_3$) alcohols;

(d) optionally one or more appropriate excipients or carriers; and (e) optionally one or more additional active ingredients.

Clause 2. The composition according to clause 1, wherein: the one or more film forming agents (a) are selected from the group consisting of (C$_1$-C$_6$)alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$) alkoxy (C$_1$-C$_6$)alkyl methacrylate based polymers; hydroxy (C$_1$-C$_6$)alkyl acrylate based polymers; hydroxy(C$_1$-C$_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers; a copolymer comprising two or more selected from the group consisting of C$_1$-C$_6$)alkyl acrylate based polymers; (C$_1$-C$_6$)alkyl methacrylate based polymers; (C$_1$-C$_6$) alkoxy (C$_1$-C$_6$)alkyl acrylate based polymers; (C$_1$-C$_6$) alkoxy (C$_1$-C$_6$)alkyl methacrylate based polymers; hydroxy (C$_1$-C$_6$)alkyl acrylate based polymers; hydroxy(C$_1$-C$_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers; a copolymer comprising one selected from $C_1$-$C_6$) alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers; hydroxy($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers and methacrylic acid; $C_1$-$C_6$) alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers; hydroxy($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers and acrylic acid: and $C_1$-$C_6$) alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers; hydroxy($C_1$-$C_6$)alkyl acrylate based polymers; hydroxy($C_1$-$C_6$)alkyl methacrylate based polymers; mono and di-acrylates of glycols and poly glycols (e.g. glycerol and polyalkylene glycols); mono and di-methacrylates of glycols and polyglycols (e.g. glycerol and polyalkylene glycols); glycidyl acrylate based polymers; and glycidyl methacrylate based polymers with acrylamide; poly(vinyl alcohol) based polymer; poly(urethane) based polymer; silicone based polymer; cellulose based polymer, and mixture thereof.

Clause 3. The composition according to any of the clauses 1 or 2, wherein the one or more film-forming agents (a) are selected from the group consisting of $(C_1$-$C_6)$alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers, hydroxy($C_1$-$C_6$)alkyl acrylate, hydroxy($C_1$-$C_6$)alkyl methacrylate; copolymers thereof; copolymers of one of $(C_1$-$C_6)$ alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers, hydroxy($C_1$-$C_6$)alkyl acrylate, hydroxy($C_1$-$C_6$)alkyl methacrylate with methacrylic acid; copolymers of one of $(C_1$-$C_6)$alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers, hydroxy($C_1$-$C_6$)alkyl acrylate, hydroxy($C_1$-$C_6$)alkyl methacrylate with acrylic acid; copolymers of one of $(C_1$-$C_6)$alkyl acrylate based polymers; $(C_1$-$C_6)$alkyl methacrylate based polymers; $(C_1$-$C_6)$alkoxy $(C_1$-$C_6)$alkyl acrylate based polymers; $(C_1$-$C_6)$alkoxy $(C_1$-$C_6)$alkyl methacrylate based polymers, hydroxy($C_1$-$C_6$)alkyl acrylate, hydroxy($C_1$-$C_6$)alkyl methacrylate with acrylamide; mono-acrylates of glycols and poly glycols; mono-methacrylates of glycols and polyglycols; glycidyl acrylate based polymers; and glycidyl methacrylate based polymers with acrylamide; and mixture thereof; particularly $(C_1$-$C_6)$ alkoxy $(C_1$-$C_6)$alkyl methacrylate based polymers.

Clause 4. The composition according to any of the clauses 1-3, wherein the one or more film-forming agents (a) are $(C_1$-$C_6)$alkoxy $(C_1$-$C_6)$alkyl methacrylate based polymer selected from the group consisting of 2-ethoxyethyl methacrylate, 2-methoxyethyl methacrylate, 2-propyl methacrylate and a mixture thereof.

Clause 5. The composition according to any of the clauses 1-4, wherein the disinfectant (b) is selected from the group consisting of $(C_1$-$C_6)$alkyl N(alpha)-($C_{10}$-$C_{25}$)alkanoyl-L-arginate or a salt thereof; chlorhexidine or a salt thereof; 2-fenoxietanol; sorbic acid and sorbate thereof; and a mixture thereof.

Clause 6. The composition according to any of the clauses 1-5, wherein the disinfectant (b) is a $(C_1$-$C_6)$alkyl N(alpha)-($C_{10}$-$C_{25}$)alkanoyl-L-arginate or a salt thereof is a $(C_1$-$C_6)$ alkyl lauroyl arginate or a salt thereof selected from ethyl lauroyl arginate and ethyl lauroyl arginate hydrochloride salt.

Clause 7. The composition according to any of the clauses 1-6, wherein the water immiscible solvent (c1) is selected from the group consisting of:

a $(C_1$-$C_5)$alkyl-CO—O—$(C_1$-$C_6)$alkyl selected from the group consisting of ethyl acetate, isopropyl acetate, n-propyl acetate, and mixture thereof; particularly ethyl acetate;

a $((C_1$-$C_6)$alkyl$)_3$Si—O—Si$((C_1$-$C_6)$alkyl$)_3$; particularly hexamethyldisiloxane; $C_1$-$C_5$)alkyl-O—$(C_2$-$C_5)$alkyl as water immiscible solvents (c1) selected from the group consisting of diethylether, diisopropylether, tert-butyl methyl ether and a mixture thereof; particularly tert-butyl methyl ether.

Clause 8. The composition according to any of the clauses 1-7, wherein the one or more $(C_2$-$C_3)$alcohols (c3) of the solvent system (c) is selected from the group consisting of ethanol, n-propanol, iso-propanol, and a mixture thereof; particularly ethanol or a mixture of ethanol and isopropanol.

Clause 9. The composition according to any of the clauses 1-8, wherein the solvent system further comprises:

(c4) one or more water-miscible solvents selected from the group consisting of water, glycol, glycerine and a mixture thereof.

Clause 10. The composition according to any of the clauses 1-9, comprising:

(a) the film forming $(C_1$-$C_6)$alkoxy $(C_1$-$C_6)$ alkyl methacrylate polymers is 2-ethoxyethyl methacrylate;

(b) the disinfectant is a ethyl lauroyl arginate or a salt thereof;

(c) the solvent system comprising:

(c1) ethyl acetate as the $(C_1$-$C_5)$alkyl-CO—O—$(C_1$-$C_6)$ alkyl water-immiscible solvent;

(c2) acetone;

(c3) a mixture of ethanol and isopropanol as $(C_2$-$C_3)$ alcohols; and (c4) optionally water, glycol, glycerine or a mixture thereof as water-miscible solvent, particularly a mixture of water and glycerine;

alternatively, (a) the film forming $(C_1$-$C_6)$alkoxy $(C_1$-$C_6)$ alkyl methacrylate polymers is 2-ethoxyethyl methacrylate;

(b) the disinfectant is a ethyl lauroyl arginate or a salt thereof;

(c) the solvent system comprising:

(c1) a mixture of ethyl acetate and hexamethyldisiloxane as water-immiscible solvent;

(c2) acetone;

(c3) isopropanol as $(C_2$-$C_3)$ alcohols; and (c4) optionally water, glycol, glycerine or a mixture thereof as water-miscible solvent, particularly a mixture of water and glycerine.

Clause 11. The composition according to any of the clauses 1-10, comprising:

(a) from 5 to 20% by weight in relation to the total weight of the composition of one or more film formings; and (b) from 0.02 to 0.40% by weight in relation to the total weight of the composition of one or more disinfectants;

particularly, (a) from 5 to 20% by weight in relation to the total weight of the composition of one or more film forming ($C_1$-$C_6$)alkoxy ($C_1$-$C_6$) alkyl methacrylate polymers, particularly 2-ethoxyethyl methacrylate; and (b) from 0.02 to 0.40% by weight in relation to the total weight of the composition of one or more ($C_1$-$C_6$)alkyl N(alpha)-($C_{10}$-$C_{25}$)alkanoyl-L-arginate disinfectants or a salt thereof.

Clause 12. The composition according to any of the clauses 1-11, comprising from 80 to 95% by weight of a solvent system (c), wherein the solvent system comprises:

(c1) from 1 to 50% by weight in relation to the total weight of the solvent system of one or more water immiscible solvents selected from the group consisting of ($C_1$-$C_5$)alkyl-CO—O—($C_1$-$C_6$)alkyl, (($C_1$-$C_6$)alkyl)$_3$ Si—O—Si(($C_1$-$C_6$)alkyl)$_3$, ($C_1$-$C_5$)alkyl-O—($C_2$-$C_5$)alkyl and a mixture thereof;

(c2) from 1 to 70% by weight in relation to the total weight of the solvent system of acetone;

(c3) from 5 to 70% by weight in relation to the total weight of the solvent system of ($C_2$-$C_3$) alcohols; and (c4) from 0 to 20% by weight in relation to the total weight of the solvent system of one or more water-miscible solvent selected from water, glycol, glycerine and a mixture thereof;

being the sum of (c1), (c2), (c3) and (c4) up to 100% by weight in relation to the total weight of the solvent system;

Clause 13. The composition according to any of the clauses 1-12, wherein the one or more appropriate excipients or carriers are selected from the group consisting of propellant, pH adjusting agent, thickening agent, gelling agent, antioxidant, fragrance, colorant, opacifying agents, and a mixture thereof; and the composition optionally further comprises one or more additional active agents; particularly selected from the group consisting of anti-inflammatory agents, anticoagulant agents, antibiotic, fungicide, viricide, sunscreen, biocide, anesthetic, analgesic, healing agents and a mixture thereof.

Clause 14. The composition according to any of the clauses 1-13, which is essentially free of phthalate containing compounds; latex containing compounds; or phthalate containing compounds and latex containing compounds; particularly free of phthalate containing compounds, latex containing compounds, or phthalate containing compounds and latex containing compounds.

Clause 15. The composition according to any of the clauses 1-14, which is a topical composition selected from the group consisting of creams, sticks, spray, soft solids, gels, mousses, ointments and pastes.

Clause 16. An adherent film, comprising:

(a) the one or more film forming agents as defined in any of the clauses 1-15; and (b) the one or more disinfectants as defined in any of the clauses 1-15;

which is obtainable in-situ by applying the composition as defined in any of the clauses 1-15 over the surface to be filmed under such conditions that allows obtaining the film;

particularly, (a) ($C_1$-$C_6$)alkoxy ($C_1$-$C_6$) alkyl methacrylate polymers as the one or more film forming agents; and (b) ($C_1$-$C_6$)alkyl N(alpha)-($C_{10}$-$C_{25}$)alkanoyl-L-arginate disinfectant or a salt thereof as the one or more disinfectants;

which is obtainable in-situ by applying the composition as defined in any of the clauses 1-15 over the surface to be filmed under such conditions that allows obtaining the film;

or particularly (a) 2-ethoxyethyl methacrylate as ($C_1$-$C_6$)alkoxy ($C_1$-$C_6$) alkyl methacrylate film forming polymer; and (b) ethyl lauroyl arginate or a salt thereof; particularly hydrochloride salt, as disinfectant.

Clause 17. The adherent film according to clause 16, comprising:

(a) from 92% to 99.95% by weight in relation to the weight of the film of one or more film forming agents as defined in any of the clauses 1-15; and (b) from 0.05 to 4% by weight in relation to the weight of the film of one or more disinfectants as defined in any of the clauses 1-15;

being the sum of the all ingredients of the film up to 100% by weight in relation to the weight of the film; particularly (a) from 92% to 99.95% by weight in relation to the weight of ($C_1$-$C_6$)alkoxy ($C_1$-$C_6$) alkyl methacrylate polymers as the one or more film forming agents; and (b) from 0.05% to 4% by weight in relation to the weight of the film of ($C_1$-$C_6$)alkyl N(alpha)-($C_{10}$-$C_{25}$)alkanoyl-L-arginate as the one or more disinfectants;

being the sum of the all ingredients of the film up to 100% by weight of the weight of the film.

Clause 18. Use of the composition as defined in any of the clauses 1-15, as film-forming agent; particularly by depositing the composition on a surface to be filmed for forming an in-situ adherent film; particularly selected from in-situ film dressing and an in-situ fixation film.

Clause 19. The composition as defined in any of the clauses 1-15; or alternatively the adherent film as defined in any of the clauses 16-18, for use in therapy; particularly in the treatment or prevention of tissue and organs injuries; particularly in the treatment and prevention of wound healing, burn healing, skin blisters, chafing, sunlight damage, insect bites, punctures and vaccinations;

or alternatively, the use of the composition as defined in any of the clauses 1-15; or alternatively the adherent film as defined in any of the clauses 16-18 in cosmetics.

Clause 20. Use of the composition as defined in any of the clauses 1-15; or alternatively the adherent film as defined in any of the clauses 16-18 as fixation agent for medical material fixation; particularly selected from drain tracks, catheter tracts, bandages and sticks; for ostomy material fixation and for organs and tissues fixation.

What is claimed is:

1. A composition comprising:

(a) one or more film forming agents;

(b) one or more disinfectants;

(c) a solvent system comprising:

(c1) one or more water immiscible solvents selected from the group consisting of ($C_1$-$C_5$)alkyl-CO—O—($C_1$-$C_6$)alkyl, (($C_1$-$C_6$)alkyl)$_3$Si—O—Si(($C_1$-$C_6$)alkyl)$_3$, ($C_1$-$C_5$)alkyl-O—($C_2$-$C_5$)alkyl and mixtures thereof;

(c2) acetone; and (c3) one or more (C$_2$-C$_3$) alcohols;

(c4) water;

(d) optionally one or more appropriate excipients or carriers; and (e) optionally one or more additional active ingredients;

wherein:

the one or more film-forming agents (a) are selected from the group consisting of (C$_1$-C$_6$)alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$) alkyl methacrylate; copolymers thereof; copolymers of one of (C$_1$-C$_6$)alkyl acrylate based polymers; (C$_1$-C$_6$) alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$)alkyl methacrylate with methacrylic acid; copolymers of one of (C$_1$-C$_6$) alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$)alkyl methacrylate with acrylic acid; copolymers of one of (C$_1$-C$_6$)alkyl acrylate based polymers; (C$_1$-C$_6$)alkyl methacrylate based polymers; (C$_1$-C$_6$)alkoxy (C$_1$-C$_6$)alkyl acrylate based polymers; (C$_1$-C$_6$)alkoxy (C$_1$-C$_6$)alkyl methacrylate based polymers, hydroxy(C$_1$-C$_6$)alkyl acrylate, hydroxy(C$_1$-C$_6$)alkyl methacrylate with acrylamide; mono-acrylates of glycols and poly glycols; mono-methacrylates of glycols and polyglycols; glycidyl acrylate based polymers; and glycidyl methacrylate based polymers with acrylamide; and the one or more disinfectants (b) are (C$_1$-C$_6$)alkyl N(alpha)-(C$_{10}$-C$_{25}$)alkanoyl-L-arginate or a salt thereof.

2. The composition according to claim 1, wherein the (C$_1$-C$_6$)alkyl N(alpha)-(C$_{10}$-C$_{25}$)alkanoyl-L-arginate or a salt thereof is (C$_1$-C$_6$)alkyl lauroyl arginate or a salt thereof.

3. The composition according to claim 2, wherein the (C$_1$-C$_6$)alkyl lauroyl arginate or a salt thereof is selected from the group consisting of ethyl lauroyl arginate and ethyl lauroyl arginate hydrochloride salt.

4. The composition according to claim 1, wherein the one or more film-forming agents are (C$_1$-C$_6$)alkoxy (C$_1$-C$_6$)alkyl methacrylate based polymers.

5. The composition according to claim 4, wherein the (C$_1$-C$_6$)alkoxy (C$_1$-C$_6$)alkyl methacrylate based polymers are selected from the group consisting of 2-ethoxyethyl methacrylate, 2-methoxyethyl methacrylate, 2-propyl methacrylate, and mixtures thereof.

6. The composition according to claim 5, wherein the (C$_1$-C$_6$)alkoxy (C$_1$-C$_6$)alkyl methacrylate based polymers are 2-ethoxyethyl methacrylate.

7. The composition according to claim 1, wherein the water immiscible solvent is selected from the group consisting of:

a (C$_1$-C$_5$)alkyl-CO—O—(C$_1$-C$_6$)alkyl selected from the group consisting of ethyl acetate, isopropyl acetate, n-propyl acetate, and mixtures thereof;

a ((C$_1$-C$_6$)alkyl)$_3$Si—O—Si((C$_1$-C$_6$)alkyl)$_3$; and a (C$_1$-C$_5$)alkyl-O—(C$_2$-C$_5$)alkyl selected from the group consisting of diethylether, diisopropylether, tert-butyl methyl ether and mixtures thereof.

8. The composition according to claim 1, wherein the one or more (C$_2$-C$_3$)alcohols of the solvent system is selected from the group consisting of ethanol, n-propanol, iso-propanol, and mixtures thereof.

9. The composition according to claim 1, comprising:

(a) the film forming (C$_1$-C$_6$)alkoxy (C$_1$-C$_6$) alkyl methacrylate polymer being 2-ethoxyethyl methacrylate;

(b) the disinfectant being ethyl lauroyl arginate or a salt thereof;

(c) the solvent system comprising:

(c1) ethyl acetate;

(c2) acetone;

(c3) a mixture of ethanol and isopropanol; and (c4) water; or alternatively, (a) the film forming (C$_1$-C$_6$)alkoxy (C$_1$-C$_6$) alkyl methacrylate polymer being 2-ethoxyethyl methacrylate;

(b) the disinfectant being ethyl lauroyl arginate or a salt thereof;

(c) the solvent system comprising:

(c1) a mixture of ethyl acetate and hexamethyldisiloxane;

(c2) acetone;

(c3) isopropanol; and (c4) water.

10. The composition according to claim 1, further comprising:

(a) from 5 to 20% by weight in relation to the total weight of the composition of one or more film forming agents; and (b) from 0.02 to 0.40% by weight in relation to the total weight of the composition of one or more disinfectants.

11. The composition according to claim 1, comprising from 80 to 95% by weight of a solvent system (c), wherein the solvent system comprises:

(c1) from 1 to 50% by weight in relation to the total weight of the solvent system of one or more water immiscible solvents selected from the group consisting of (C$_1$-C$_5$)alkyl-CO—O—(C$_1$-C$_6$)alkyl, ((C$_1$-C$_6$)alkyl)$_3$Si—O—Si((C$_1$-C$_6$)alkyl)$_3$, (C$_1$-C$_5$)alkyl-O—(C$_2$-C$_5$)alkyl and mixtures thereof;

(c2) from 1 to 70% by weight in relation to the total weight of the solvent system of acetone;

(c3) from 5 to 70% by weight in relation to the total weight of the solvent system of (C$_2$-C$_3$) alcohols; and (c4) up to 20% by weight in relation to the total weight of water; being the sum of (c1), (c2), (c3) and (c4) up to 100% by weight in relation to the total weight of the solvent system.

12. The composition according to claim 1, wherein the one or more appropriate excipients or carriers are selected from the group consisting of propellant, pH adjusting agent, thickening agent, gelling agent, antioxidant, fragrance, colorant, opacifying agents, and mixtures thereof; and the composition optionally further comprises one or more additional active agents.

13. The composition according to claim 1, which is essentially free of phthalate containing compounds; latex containing compounds; or phthalate containing compounds and latex containing compounds.

14. The composition according to claim 1, which is a topical composition selected from the group consisting of creams, sticks, spray, soft solids, gels, mousses, ointments and pastes.

15. An adherent film, comprising:

(a) one or more film forming agents selected from the group consisting of (C$_1$-C$_6$)alkyl acrylate based polymers; (C$_1$-C$_6$)alkyl methacrylate based polymers; (C$_1$-$C_6$)alkoxy ($C_1$-$C_6$)alkyl acrylate based polymers; ($C_1$-$C_6$)alkoxy ($C_1$-$C_6$)alkyl methacrylate based polymers, hydroxy($C_1$-$C_6$)alkyl acrylate, hydroxy($C_1$-$C_6$)alkyl methacrylate; copolymers thereof; copolymers of one of ($C_1$-$C_6$)alkyl acrylate based polymers; ($C_1$-$C_6$)alkyl methacrylate based polymers; ($C_1$-$C_6$)alkoxy ($C_1$-$C_6$) alkyl acrylate based polymers; ($C_1$-$C_6$)alkoxy ($C_1$-$C_6$) alkyl methacrylate based polymers, hydroxy($C_1$-$C_6$) alkyl acrylate, hydroxy($C_1$-$C_6$)alkyl methacrylate with methacrylic acid; copolymers of one of ($C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$)alkoxy ($C_1$-$C_6$)alkyl methacrylate based polymers, hydroxy($C_1$-$C_6$)alkyl acrylate, hydroxy($C_1$-$C_6$)alkyl methacrylate with acrylic acid; copolymers of one of ($C_1$-$C_6$)alkyl acrylate based polymers; ($C_1$-$C_6$)alkyl methacrylate based polymers; ($C_1$-$C_6$)alkoxy ($C_1$-$C_6$)alkyl acrylate based polymers; ($C_1$-$C_6$)alkoxy ($C_1$-$C_6$)alkyl methacrylate based polymers, hydroxy($C_1$-$C_6$)alkyl acrylate, hydroxy($C_1$-$C_6$) alkyl methacrylate with acrylamide; mono-acrylates of glycols and poly glycols; mono-methacrylates of glycols and polyglycols; glycidyl acrylate based polymers; and glycidyl methacrylate based polymers with acrylamide; and

(b) one or more disinfectants being ($C_1$-$C_6$)alkyl N(alpha)-($C_{10}$-$C_{25}$)alkanoyl-L-arginate or a salt thereof; which is obtainable in-situ by applying the composition as defined in claim 1 over the surface to be filmed under such conditions that allows obtaining the film.

16. The adherent film according to claim 15, comprising:
(a) from 92% to 99.95% by weight in relation to the weight of the film of one or more film forming agents; and
(b) from 0.05 to 4% by weight in relation to the weight of the film of one or more disinfectants; being the sum of all ingredients of the film up to 100% by weight in relation to the weight of the film.

17. A method of using the composition as defined in claim 1, the method comprising depositing the composition on a surface to be filmed and forming an in-situ adherent film.

18. A method of using the composition as defined in claim 1 as fixation agent for medical material fixation, the method comprising depositing the composition on a surface to be filmed and forming an in-situ fixation film.

19. The method of using according to claim 18, wherein the medical material is selected from the group consisting of drain tracks, catheter tracts, bandages and sticks, ostomy materials, and materials for organ and tissue fixation.

* * * * *